(12) United States Patent
Nakashima et al.

(10) Patent No.: US 6,638,620 B2
(45) Date of Patent: Oct. 28, 2003

(54) REVERSIBLE THERMOCHROMIC COMPOSITION HAVING IMPROVED LIGHT-FASTNESS AND PRODUCT COMPRISING SAME

(75) Inventors: Akio Nakashima, Aichi (JP); Yoshiaki Ono, Aichi (JP)

(73) Assignee: The Pilot Ink Co., Ltd., Aichi (JP)

( * ) Notice: Subject to any disclaimer, the term of this patent is extended or adjusted under 35 U.S.C. 154(b) by 0 days.

(21) Appl. No.: 09/923,537

(22) Filed: Aug. 8, 2001

(65) Prior Publication Data

US 2002/0063244 A1 May 30, 2002

(30) Foreign Application Priority Data

Aug. 9, 2000 (JP) ........................................ 2000-275649

(51) Int. Cl.[7] ............................ B32B 9/00; B32B 15/04; C09D 11/00
(52) U.S. Cl. ............................ 428/402.2; 428/402.24; 428/411.1; 106/31.18
(58) Field of Search .................... 106/31.18; 428/320.2, 428/321.5, 364, 375, 402.2, 402.24, 411.1

(56) References Cited

U.S. PATENT DOCUMENTS

| 3,560,229 A | 2/1971 | Farnham et al. | 106/21 |
| 4,028,118 A | 6/1977 | Nakasuji et al. | 106/21 |
| 5,879,438 A | 3/1999 | Fujita et al. | 106/31.18 |

FOREIGN PATENT DOCUMENTS

| EP | 0 659 582 A1 | 6/1995 |
| EP | 0 908 501 A1 | 4/1999 |
| FR | 2 503 729 | 10/1982 |
| JP | 6-59746 | 8/1994 |
| JP | 11-131058 | 5/1999 |
| JP | 11-166123 | 6/1999 |

OTHER PUBLICATIONS

European Search Report dated Nov. 29, 2001.

*Primary Examiner*—Ramsey Zacharia
(74) *Attorney, Agent, or Firm*—Sughrue Mion, PLLC

(57) ABSTRACT

A reversible thermochromic composition which can be freely adjusted in its discoloration temperature even if the kind of electron donating compound and electron accepting compound to be used in combination remain the same and exhibits a remarkably improved light-fastness during quenching. A reversible thermochromic composition having an improved light-fastness comprising (a) an electron donating compound, (b) an electron accepting compound ultraviolet absorbing capacity represented by the following general formula I:

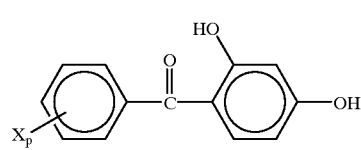

(I)

wherein X represents a hydrogen atom, $-C_nH_{2n+1}$ or $-OC_mH_{2m+1}$; m represents an integer of from 1 to 9; n represents an integer of from 1 to 10; and p represents an integer of from 1 to 3, and (c) a discoloration temperature adjustor and a product comprising same.

9 Claims, 2 Drawing Sheets

REVERSIBLE THERMOCHROMIC COMPOSITION HAVING IMPROVED LIGHT-FASTNESS AND PRODUCT COMPRISING SAME

FIELD OF THE INVENTION

The present invention relates to a reversible thermochromic composition having an excellent discoloration sensitivity, which comprises a special electron accepting compound having ultraviolet absorbing capacity to exhibit an improved light-fastness, particularly during quenching, without impairing discoloration sensitivity and a product comprising same.

BACKGROUND ART

A thermochromic composition comprising an electron donating compound and an electron accepting compound in combination is known as disclosed in U.S. Pat. No. 3,560,229. Since the discoloration temperature of this composition is determined by the kind of the two compounds to be combined, it is very difficult to obtain a composition which can undergo discoloration at a desired temperature.

In order to solve this problem, the inventors proposed an invention which comprises using a specific alcohol, ester or ketone as a discoloration temperature adjustor to adjust the discoloration temperature to a desired value even when the kind of electron donating compound and electron accepting compound to be used in combination remain the same (U.S. Pat. No. 4,028,118, JP-B-6-59746 (The term "JP-B" as used herein means an "examined Japanese patent application")).

The inventors further invented a process which comprises using a special light-fastness providing agent and light stabilizer having electron acceptingness to improve the light-fastness of a reversible thermochromic composition in quenched state (U.S. Pat. No. 5,879,438).

The above proposed invention can attain free adjustment of discoloration temperature even when the kind of electron donating compound and electron accepting compound to be used in combination remain the same and exerts an excellent effect of remarkably improving light-fastness in quenched state. However, as the added amount of the light stabilizer increases, the discoloration sensitivity tends to fall. Therefore, the above cited invention is limited in its practical use.

The present invention provides a reversible thermochromic composition which can be freely adjusted in its discoloration temperature even if the kind of electron donating compound and electron accepting compound to be used in combination remain the same and exhibits a remarkably improved light-fastness during quenching.

SUMMARY OF THE INVENTION

The present invention lies in the following constitutions:

1. A reversible thermochromic composition having an improved light-fastness, which comprises
   (a) an electron donating compound,
   (b) an electron accepting compound having ultraviolet absorbing capacity which is represented by the following general formula I:

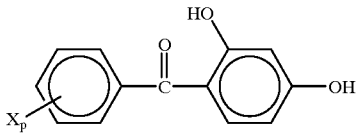

wherein X represents a hydrogen atom, —$C_nH_{2n+1}$ or —$OC_mH_{2m+1}$; m represents an integer of from 1 to 9; n represents an integer of from 1 to 10; and p represents an integer of from 1 to 3, and
   (c) a discoloration temperature adjustor.

2. A reversible thermochromic composition having an improved light-fastness, which comprises
   (a) an electron donating compound,
   (b) an electron accepting compound having ultraviolet absorbing capacity which is represented by the following general formula I:

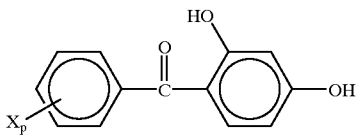

wherein X represents a hydrogen atom, —$C_nH_{2n+1}$ or —$OC_mH_{2m+1}$; m represents an integer of from 1 to 9; n represents an integer of from 1 to 10; and p represents an integer of from 1 to 3,
   (c) a discoloration temperature adjustor, and
   (d) an electron accepting light-fastness providing agent represented by the following general formula II:

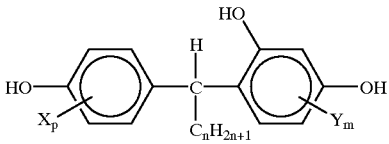

wherein n represents an integer of from 5 to 17 (straight-chain and branched); X represents a $C_1$–$C_4$ straight-chain or branched hydrocarbon or halogen; Y represents a $C_1$–$C_4$ straight-chain or branched hydrocarbon or halogen; p represents an integer of from 0 to 3; and m represents an integer of from 0 to 3.

3. A reversible thermochromic composition having an improved light-fastness, which comprises
   (a) an electron donating compound,
   (b) an electron accepting compound having ultraviolet absorbing capacity represented by the following general formula I:

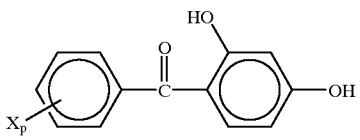

wherein X represents a hydrogen atom, —$C_nH_{2n+1}$ or —$OC_mH_{2m+1}$; m represents an integer of from 1 to 9; n represents an integer of from 1 to 10; and p represents an integer of from 1 to 3,
   (c) a discoloration temperature adjustor,
   (d) an electron accepting light-fastness providing agent represented by the following general formula II:

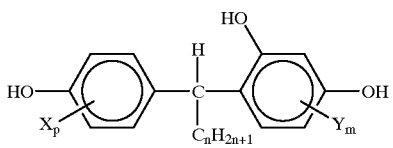

wherein n represents an integer of from 5 to 17 (straight-chain and branched); X represents a $C_1$–$C_4$ straight-chain or branched hydrocarbon or halogen; Y represents a $C_1$–$C_4$ straight-chain or branched hydrocarbon or halogen; p represents an integer of from 0 to 3; and m represents an integer of from 0 to 3, and (e) a light stabilizer.

4. The reversible thermochromic composition having an improved light-fastness according to any one of Clauses 1 to 3, which further comprises a microcapsule incorporating said reversible thermochromic composition therein.

5. The reversible thermochromic composition having an improved light-fastness according to any one of Clauses 1 to 4, which further comprises a color developer blended in said reversible thermochromic composition having an improved light-fastness.

6. The reversible thermochromic composition having an improved light-fastness according to Clause 5, wherein said color developer is a binder.

7. A molding resin composition comprising a synthetic resin and a reversible thermochromic composition according to any one of Clauses 1 to 4 blended therein.

8. A reversible thermochromic yarn comprising a reversible thermochromic composition according to any one of Clauses 1 to 4 and a thermoplastic resin.

9. A reversible thermochromic layer having an improved light-fastness according to any one of Clauses 1 to 8, which further comprises (f) a layer of light stabilizer and/or metallic luster pigment provided on the surface of a layer formed by a reversible thermochromic composition.

Figure 1:
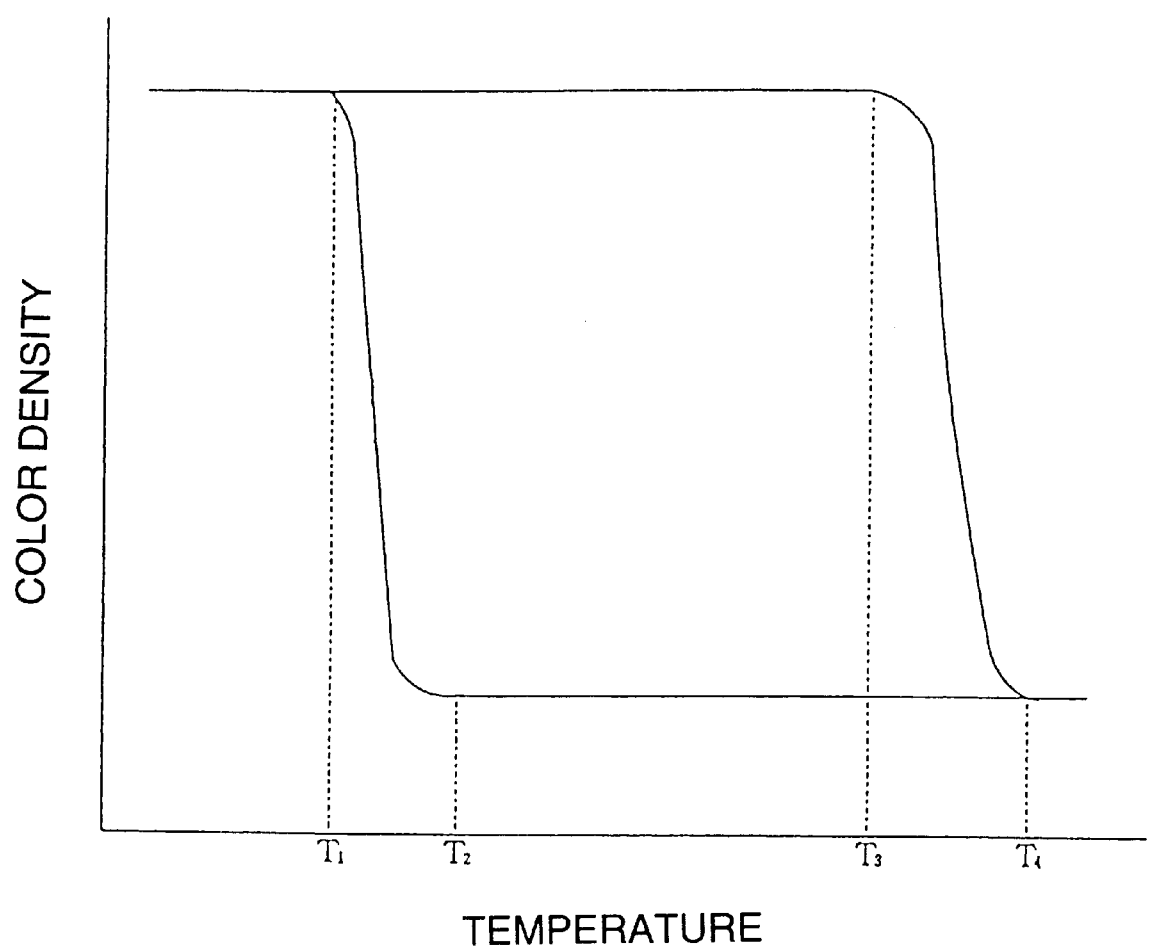
FIG. 1 is a graph illustrating hysteresis characteristics on color density-temperature curve of a reversible thermochromic composition according to the invention.

The reference numerals in the figures have the following meanings.

| | |
|---|---|
| $T_1$ | Full color development temperature |
| $T_2$ | Color development starting temperature |
| $T_3$ | Quenching starting temperature |
| $T_4$ | Full quenching temperature |

DETAILED DESCRIPTION OF THE INVENTION

The present invention lies in a reversible thermochromic composition having an improved light-fastness in quenched state comprising an electron donating compound (a), an electron accepting compound having ultraviolet absorbing capacity and a discoloration temperature adjustor (c) and thus is characterized by the use of an electron accepting compound having ultraviolet absorbing capacity that provides a remarkable improvement of light-fastness in quenched state without impairing discoloration sensitivity.

A representative example of the electron donating compound is a leuco dye. However, since a leuco dye exhibits a poor light-fastness, a composition comprising such a dye ages when irradiated with light and shows deteriorated discolorability.

With reference to leuco dye, when provided with electron, i.e., placed in color-developed state, an electron donating compound can be greatly affected by visible light or indirect light to show deteriorated light-fastness and hence deteriorated discolorability.

On the other hand, when placed in quenched state, i.e., being not ionized, the electron donating compound is in the form of colorless molecular state and thus is greatly affected by ultraviolet rays to show a remarkably deteriorated discolorability. The thermochromic composition undergoes color development and quenching to perform display. Accordingly, light-fastness in quenched state, too, is important.

The color-developed state and quenched state of the thermochromic composition will be described hereinafter.

All the electron donating compound, the electron accepting compound and the discoloration temperature adjustor constituting the thermochromic composition are molecular compounds which are not ionized when actually handled. When the ambient temperature is not higher than the discoloration temperature, a reversible thermochromic composition having these components uniformly mixed with each other causes the electron donating compound and the electron accepting compound to be ionized and bonded to each other, making color development.

It is thought that in transient period during discoloration, the electron donating compound and the electron accepting compound are placed in between ionized state and molecular state and in somewhat ionized state, i.e., bonded to each other slightly ionically. Even when slightly ionized, color development occurs. Thus, some problem with light-fastness in color-developed state arises. Accordingly, transient state is considered color-developed state in respect to light-fastness.

On the contrary, when the ambient temperature is not lower than the discoloration temperature, the ionical bonding of the electron donating compound to the electron accepting compound disappears. These compounds then become molecular to cause quenching.

Accordingly, the blocking of ultraviolet rays by the addition of a light stabilizer to a reversible thermochromic composition the electron donating compound and electron accepting compound of which are molecular to develop quenched state is an exceptionally useful method for improving light-fastness in quenched state. However, as the added amount of the light stabilizer increases, the discoloration sensitivity decreases, making it more difficult to show sharp discoloration. Therefore, this method can be hardly effected on a practical basis depending on the purpose.

The electron accepting compound having ultraviolet absorbing capacity represented by the general formula I to be used in the invention has electron attraction properties itself.

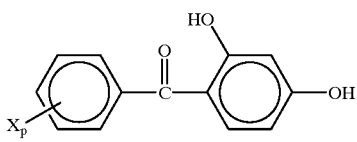

(I)

wherein X represents a hydrogen atom, —$C_nH_{2n+1}$ or —$OC_mH_{2m+1}$; m represents an integer of from 1 to 9; n represents an integer of from 1 to 10; and p represents an integer of from 1 to 3.

In addition to action of receiving an electron donating compound and electron, the foregoing electron accepting compound having ultraviolet absorbing capacity exerts a special effect. In other words, the foregoing electron accepting compound having ultraviolet absorbing capacity absorbs ultraviolet rays, which have the greatest effect on light-fastness in quenched state, to become excited and then undergoes stable non-radiation deactivation from excited state to release energy and return to the ground state. This process of absorbing ultraviolet rays and releasing energy is repeated. At the same time, since this electron donating compound has a high acidity due to the electron accepting properties of the ultraviolet absorbing group, it undergoes excellent reaction of providing and receiving electron, making it possible to provide a reversible thermochromic composition which attains both improved light-fastness in quenched state and excellent discoloration sensitivity which could not be attained by the conventional process involving the addition of a light stabilizer.

In the electron accepting compound having ultraviolet absorbing capacity represented by the general formula I, n is an integer of from 1 to 10, and m is an integer of from 1 to 9. When n is greater than 10 or m is greater than 9, the resulting electron accepting compound exhibits too great a solubility in the component (c) and thus tends to have a discoloration sensitivity drop, making it difficult to provide a reversible thermochromic composition which attains both improved light-fastness in quenched state and excellent discoloration sensitivity.

As the electron accepting compound there may be used the electron accepting compound having ultraviolet absorbing capacity (b) alone. However, other electron accepting compounds may be used as well.

In the case where the electron accepting compound having ultraviolet absorbing capacity is used in combination with other electron accepting compounds, the amount of the electron accepting compound having ultraviolet absorbing capacity to be used is not smaller than 5% by weight, preferably not smaller than 10%, of the total amount of electron accepting compounds used.

When the proportion of the electron accepting compound having ultraviolet absorbing capacity is not greater than 5% by weight, the electron accepting compound having ultraviolet absorbing capacity cannot exert the foregoing special effect.

As other electron accepting compounds to be used in combination with the electron accepting compound having ultraviolet absorbing capacity, there are preferably used electron accepting light-fastness providing agents.

The electron accepting light-fastness providing agent (d) represented by the general formula II to be used in the invention is a bisphenol compound or bis(hydroxyphenyl) compound containing an alkyl group and two phenyl rings each having a hydroxyl group, which is represented by the following general formula II:

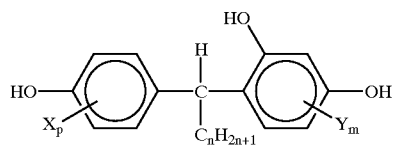

(II)

wherein n represents an integer of from 5 to 17 (straight-chain and branched); X represents a $C_1$–$C_4$ straight-chain or branched hydrocarbon or halogen; Y represents a $C_1$–$C_4$ straight-chain or branched hydrocarbon or halogen; p represents an integer of from 0 to 3; and m represents an integer of from 0 to 3. The alkyl moiety in the foregoing compound has from 5 to 17 carbon atoms. When the number of carbon atoms in the alkyl moiety falls below 5, the resulting light-fastness providing agent has a short alkyl moiety and hence an insufficient solubility in the discoloration temperature adjustor (c) that makes it impossible to provide a sufficient stable structure in a solid atmosphere at a temperature of not higher than the discoloration temperature. On the contrary, when the number of carbon atoms in the alkyl moiety exceeds 17, the resulting light-fastness providing agent has too long an alkyl moiety and hence too great a solubility in the discoloration temperature adjustor that weakens the color assuming power and deteriorates the discoloration sensitivity to disadvantage from the practical standpoint of view.

Most preferably, the alkyl group is a straight-chain alkyl group. The branches, if any, are preferably short.

The phenyl ring may have substituents such as straight-chain or branched alkyl group and halogen. In this case, the resulting light-fastness remains almost the same so far as the alkyl group to which the phenyl group is attached is as defined above.

Examples of other electron accepting compounds which can be used in combination with the electron accepting compound having ultraviolet absorbing capacity (b) include compounds having active proton, pseudo-acidic compounds (compounds which are not acids but act as an acid in the composition to allow the color development of the compound (a)), and compounds having electron holes.

Compounds having a phenolic hydroxyl group can exhibit the most effective thermochromic characteristics. However, there may be used compounds selected from the group consisting of aromatic carboxylic acids, $C_2$–$C_5$ aliphatic carboxylic acids, metal salt of carboxylic acids, acidic phosphoric acid esters, metal salt thereof, 1,2,3-triazole, derivatives thereof, thiourea, derivatives thereof, urea, derivatives thereof, guanidine, derivatives thereof, aromatic carboxylic anhydride, aliphatic carboxylic anhydride, boric acid esters, halogenated alcohol, oxazole, thiazole, imidazole, pyrazole, pyrrole, aromatic sulfonamides, and aromatic sulfonimides.

The reversible thermochromic composition comprising an electron donating compound (a), an electron accepting compound having ultraviolet absorbing capacity (b) and a discoloration temperature adjustor (c) of the invention absorbs ultraviolet rays, which have the greatest effect on light-fastness when the electron accepting compound having ultraviolet absorbing capacity (b) is in quenched state, and undergoes non-radiation deactivation to release energy, making it possible to provide better light-fastness in quenched state than the conventional reversible thermochromic composition. The further incorporation of a light-fastness providing agent (d) causes the electron donating compound (a) to have a weak interaction with the electron accepting compound having ultraviolet absorbing capacity (b) and the light-fastness providing agent (d) and become stabilized while being dissolved in the discoloration temperature adjustor (c) in quenched state, making it possible to inhibit photo-oxidation or photodecomposition caused by light and hence further improve light-fastness in quenched state.

Referring to light-fastness in color-developed state by the light-fastness providing agent, the ionized state of the electron donating compound and the light-fastness providing agent having a long-chain alkyl group (d) can be stabilized to give a strong interaction, making it possible to improve light-fastness in quenched state in the discoloration temperature adjustor (c), which has a strong aliphatic atmosphere.

Further, the presence of a light stabilizer (e) in the reversible thermochromic composition comprising the components (a), (b), (c) and (d) gives an enhanced stabilizing effect that makes it possible to further improve light-fastness in quenched state.

The present invention also relates to a reversible thermochromic layer having a remarkably improved light-fastness in quenched state obtained by providing a layer of light stabilizer or metallic luster pigment (f) on the surface of the layer formed by the thermochromic composition of the invention. This thermochromic layer is very excellent also in discoloration sensitivity. In color-developed state, too, the light stabilizer layer or metallic lust pigment layer blocks ultraviolet rays or visible light to improve light-fastness.

The reversible thermochromic composition of the invention comprises an electron donating compound (a), an electron accepting compound having ultraviolet absorbing capacity (b), and a discoloration temperature adjustor (c). As previously mentioned, the reversible thermochromic composition of the invention may further comprise an electron accepting light-fastness providing agent (d) and a light stabilizer (e) singly or in combination. The reversible thermochromic composition of the invention may further comprise other electron accepting compounds.

The use of the electron accepting compound having ultraviolet absorbing capacity (b) makes it possible to improve discoloration sensitivity. The academic analysis of this mechanism is not necessarily sufficiently made. Judging from the repeatable and reproducible results, the inventor thinks that the special electron accepting group in the electron accepting compound having ultraviolet absorbing capacity (b) causes the acidity to rise and hence improves discoloration sensitivity.

Compounds employable in the invention will be exemplified below.

As the electron donating compound which acts as the component (a) there may be used any of those listed in Tables 1 and 2 below.

TABLE 1

| Compound group | Name of compound |
| --- | --- |
| Diphenylmethane phthalides | 3,3-Bis(p-dimethylaminophenyl)-6-dimethylaminophthalide |
| | 3,3-Bis(p-dimethylaminophenyl)phthalide, etc. |
| Phenylindolyl phthalides | 3-(4-Diethylaminophenyl)-3-(1-ethyl-2-methylindol-3-yl)phthalide |
| | 3-(2-Methyl-4-diethylamino)phenyl-3-[1-(2-methoxyethyl)-2-methylindol-3-yl]phthalide, etc. |
| Indolyl phtahlides | 3,3-Bis(1-n-butyl-2-methylindol-3-yl)phthalide |
| | 3,3-Bis(1-ethyl-2-methylindol-3-yl)phthalide |
| | 3,3-Bis(1-n-pentyl-2-methylindol-3-yl)phthalide |
| | 3-(1-n-butyl-2-methyl-indol-3-yl)-3-(1-n-octyl-2-methyl-indol-3-yl)phthalide, etc. |
| Diphenylmethane azaphthalides | 3,3-Bis(2-ethoxy-4-diethylaminophenyl)-4-azaphthalide, etc. |
| Phenylindolyl azaphthalizes | 3-(2-ethoxy-4-diethylaminophenyl)-3-(1-ethyl-2-methylindol-3-yl)-4-azaphthalide |
| | 3-(4-diethylamino-2-methylphenyl)-3-(1-ethyl-2-methylindol-3-yl)-4-azaphthalide |
| | 3-[2-ethoxy-4-(N-ethylanilino)phenyl]-3-(1-ethyl-2-methylindol-3-yl)-4-azaphthalide |
| | 3-[2-ethoxy-4-(N-ethyl-N-4-n-butylphenylamino)phenyl]-3-(1-ethyl-2-methylindol-3-yl)-7-azaphthalide, etc. |
| Fluoraones | 3,6-Dimethoxyfluorane |
| | 3,6-Di-n-butoxyfluorane |
| | 2-Chloro-6-diethylaminofluorane |
| | 2-Methyl-6-diethylaminofluorane |
| | 2-Methyl-6-(N-ethyl-N-p-tolylamino)fluorane |
| | 3-Chloro-6-cyclohexylaminofluorane |
| | 2-Methyl-6-cyclohexylaminofluorane |
| | 2-Anilino-6-(N-ethyl-N-n-hexylamino)fluorane |
| | 2-(2-Chloroanilino)-6-dimethylaminofluorane |
| | 2-(2-Chloroanilino)-6-di-n-butylaminofluorane |
| | 2-(3-Trifluoromethylanilino)-6-diethylaminofluorane |
| | 2(N-cyclohexyl-N-benzylamino)-6-diethylaminofluorane |
| | 2-N,N-dibenzylamino-6-diethylaminofluorane |
| | 2-(N-methylanilino)-6-(N-ethyl-N-p-tolylamino)fluorane |
| | 1,3-Dimethyl-6-diethylaminofluorane |
| | 2-Chloro-3-methyl-6-diethylaminofluorane |
| | 2-Chloro-3-methyl-6-(4-di-n-butylaminoanilino)fluorane |
| | 2-n-Octylamino-3-methyl-6-diethylaminofluorane |
| | 2-N,N-dibenzylamino-3-methyl-6-diethylaminofluorane |
| | 2-N,N-dibenzylamino-4-methyl-6-diethylaminofluorane |
| | 2-Anilino-3-methyl-6-(N-methyl-N-n-propylamino)fluorane |
| | 2-Anilino-3-methyl-6-diethylaminofluorane |

TABLE 1-continued

| Compound group | Name of compound |
|---|---|
| | 2-Anilino-3-methyl-6-(N-ethyl-N-isobutylamino)fluorane |
| | 2-Anilino-3-methyl-6-di-n-butylaminofluorane |
| | 2-Anilino-3-methyl-6-(N-ethyl-N-isopentylamino)fluorane |
| | 2-Anilino-3-methyl-6-di-n-pentylaminofluorane |
| | 2-Anilino-3-methyl-6-(N-methyl-N-cyclohexylamino)fluorane |
| | 2-Anilino-3-methyl-6-(N-ethyl-N-p-tolylamino)fluorane |

TABLE 2

| Compound group | Name of compound |
|---|---|
| Fluoranes (continued from above) | 2-(2-fluoroanilino)-6-di-n-butylaminofluorane |
| | 2-Xylidino-3-methyl-6-diethylaminofluorane |
| | 2-(p-n-Butylanilino)-3-methyl-6-diethylaminofluorane |
| | 1,2-Benz-6-diethylaminofluorane |
| | 1,2-Benz-6-(N-ethyl-N-isobutylamino)fluorane |
| | 1,2-Benz-6-(N-ethyl-N-isoamylamino)fluorane |
| | 1,2-Benz-6-di-n-butylaminofluorane, etc. |
| Styrylguinolines | 2-(3-Methoxy-4-dodecoxystyryl)guinoline, etc. |
| Pyridines | 4-(4-N-methyl-N-benzylaminophenyl)pyridine |
| | 2,6-Diphenyl-4-(4-dimethylaminophenyl)pyridine |
| | 2,6-Bis(4-methoxyphenyl)-4-(4-dimethylaminophenyl)pyridine |
| | 2,6-Dimethyl-3,5-biscarboethoxy-4-(4-dimethylaminophenyl)pyridine |
| | 2-(2-octoxyphenyl)-4-(4-dimethylaminophenyl)-6-phenylpyridine |
| | 2,6-Diethoxy-4-(4-diethylaminophenyl)pyridine |
| | 2,6-Bis(4-n-butoxyphenyl)-4-(4-dimethylaminophenyl)pyridine |
| | 2,6-Bis(2-n-butoxyphenyl)-4-(4-dimethylaminophenyl)pyridine |
| | 2,6-Bis(2-ethoxyphenyl)-4-(4-dimethylaminophenyl)pyridine |
| | 2,6-Bis(2-ethoxyphenyl)-4-(4-diethylaminophenyl)pyridine, etc. |
| Quinazolines | 2-(4-Dimethylaminophenyl)-4-methoxyquinazoline |
| | 2-(4-Dimethylaminophenyl)-4-phenoxyquinazoline |
| | 2-(4-Dimethylaminophenyl)-4-(4-nitrophenyloxy)quinazoline |
| | 2-(4-N-methylanilinophenyl)-4-phenoxyquinazoline |
| | 2-(4-Piperidinophenyl)-4-phenoxyquinazoline |
| | 2-(4-Dimethylaminophenyl)-4-(4-chlorophenyloxy)quinazoline |
| | 2-(4-Dimethylaminophenyl)-4-(4-methoxyphenyloxy)guinazoline, etc. |
| Bisquinazolines | 4,4'-(Ethylenedioxy)-bis[2-(4-diethylaminophenyl)quinazoline] |
| | 4,4'-[Propylenedioxy(1,3)]-bis[2-(4-diethylaminophenyl)quinazoline |
| | 4,4'-[Butylenedioxy(1,3)]-bis[2-(4-diethylaminophenyl)quinazoline |
| | 4,4'-[Butylenedioxy(1,4)]-bis[2-(4-diethylaminophenyl)quinazoline |
| | 4,4'-(Oxydiethylenedioxy)-bis[2-(4-diethylaminophenyl)quinazoline |
| | 4,4'-(Ethylenedioxy)-bis[2-(4-piperidinophenyl)quinazoline |
| | 4,4'-(Ethylenedioxy)-bis[2-(4-di-n-propylaminophenyl)quinazoline |
| | 4,4'-(Ethylenedioxy)-bis[2-(4-di-n-butylaminophenyl)quinazoline |
| | 4,4'-(Cyclohexylenedioxy)-bis[2-(4-diethylaminophenyl)guinazoline, etc. |
| Ethylenophthalides | 3,3-Bis[1,1-bis-(p-dimethylaminophenyl)ethyleno-2]phthalide |
| | 3,3-Bis[1,1-bis-(2-methyl-4-dimethylaminophenyl)ethyleno-2]phthalide |
| | 3,3-Bis[1,1-bis-(p-dimethylaminophenyl)ethyleno-2]-4,5,6,7-tetrachlorophthalide, etc. |
| Ethylenoazaphthalides | 3,3-Bis[1,1-bis-(p-dimethylaminophenyl)ethyleno-2]-4-azaphthalide |
| | 3,3-Bis[1,1-bis-(p-dimethylaminophenyl)ethyleno-2]-4,7-diazaphthalide |
| | 3-(p-Dimethylaminophenyl)-3-[1,1-bis-(p-dimethylaminophenyl)ethyleno-2]-4-azaphthalide, etc. |
| Fluorenes | 3,6-Bis(dimethylamino)fluorenespiro(3,3')-6'-dimethylaminophthalide |
| | 3,6-Bis(diethylamino)fluorenespiro(3,3')-4'-azaphthalide |
| | 3,6-Bis(diethylamino)fluorenespiro(3,3')-7'-azaphthalide |
| | 3,6-Bis(diethylamino)fluorenespiro(3,3')-4',7'-diazaphthalide, etc. |

As the electron accepting compound having ultraviolet absorbing capacity which acts as the component (b) there may be preferably used any of those listed in Table 3 below.

TABLE 3

| Compound group | Name of compound |
|---|---|
| Unsubstituted type Alkyl-substituted type | 2,4-Dihydroxybenzophenone |
| Mono-substituted | 2,4-Dihydroxy-2'-methylbenzophenone |
| | 2,4-Dihydroxy-3'-methylbenzophenone |

TABLE 3-continued

| Compound group | Name of compound |
|---|---|
| | 2,4-Dihydroxy-4'-methylbenzophenone |
| | 2,4-Dihydroxy-4'-ethylbenzophenone |
| | 2,4-Dihydroxy-4'-n-propylbenzophenone |
| | 2,4-Dihydroxy-4'-isopropylbenzophenone |
| | 2,4-Dihydroxy-4'-n-butylbenzophenone |
| | 2,4-Dihydroxy-4'-isobutylbenzophenone |

TABLE 3-continued

| Compound group | Name of compound |
| --- | --- |
| | 2,4-Dihydroxy-4'-tert-butylbenzophenone |
| | 2,4-Dihydroxy-4'-n-pentylbenzophenone |
| | 2,4-Dihydroxy-4'-n-hexylbenzophenone |
| | 2,4-Dihydroxy-4'-n-heptylbenzophenone |
| | 2,4-Dihydroxy-4'-n-octylbenzophenone |
| | 2,4-Dihydroxy-4'-n-decylbenzophenone, etc. |
| Di-substituted | 2,4-Dihydroxy-2',3'-dimethylbenzophenone |
| | 2,4-Dihydroxy-2',4'-dimethylbenzophenone |
| | 2,4-Dihydroxy-2',5'-dimethylbenzophenone |
| | 2,4-Dihydroxy-2',6'-dimethylbenzophenone |
| | 2,4-Dihydroxy-3',4'-dimethylbenzophenone |
| | 2,4-Dihydroxy-3',5'-dimethylbenzophenone, etc. |
| Tri-substituted | 2,4-Dihydroxy-2',4',6'-trimethylbenzophenone, etc. |
| Alkoxy-substituted type | |
| Mono-substituted | 2,4-Dihydroxy-2'-methoxybenzophenone |
| | 2,4-Dihydroxy-3'-methoxybenzophenone |
| | 2,4-Dihydroxy-4'-methoxybenzophenone |
| | 2,4-Dihydroxy-2'-ethoxybenzophenone |
| | 2,4-Dihydroxy-4'-ethoxybenzophenone |
| | 2,4-Dihydroxy-4'-n-propoxybenzophenone |
| | 2,4-Dihydroxy-4'-isopropoxybenzophenone |
| | 2,4-Dihydroxy-4'-isobutylbenzophenone |
| | 2,4-Dihydroxy-4'-n-butoxybenzophenone |
| | 2,4-Dihydroxy-4'-n-pentyloxybenzophenone |
| | 2,4-Dihydroxy-4'-n-hexyloxybenzophenone |
| | 2,4-Dihydroxy-4'-n-heptyloxybenzophenone |
| | 2,4-Dihydroxy-4'-n-octyloxybenzophenone |
| | 2,4-Dihydroxy-4'-n-nonyloxybenzophenone, etc. |
| Di-substituted | 2,4-Dihydroxy-2',3'-dimethoxybenzophenone |
| | 2,4-Dihydroxy-2',4'-dimethoxybenzophenone |
| | 2,4-Dihydroxy-2',5'-dimethoxybenzophenone |
| | 2,4-Dihydroxy-2',6'-dimethoxybenzophenone |
| | 2,4-Dihydroxy-3',4'-dimethoxybenzophenone |
| | 2,4-Dihydroxy-3',5'-dimethoxybenzophenone |
| | 2,4-Dihydroxy-3',4'-dimethoxybenzophenone, etc. |
| Tri-substituted | 2,4-Dihydroxy-2',3',4'-trimethoxybenzophenone |
| | 2,4-Dihydroxy-2',3',6'-trimethoxybenzophenone |
| | 2,4-Dihydroxy-3',4',5'-trimethoxybenzophenone |
| | 2,4-Dihydroxy-3',4',5'-triethoxybenzophenone, etc. |

As the discoloration temperature adjustor which acts as the component (c) there is preferably used any of those listed in Tables 4 to 10.

TABLE 4

| Compound group | Name of compound |
| --- | --- |
| (Alcohols) Monovalent aliphatic saturated alcohol having 10 or more carbon atoms | Decyl alcohol |
| | Undecyl alcohol |
| | Dodecyl alcohol |
| | Tridecyl alcohol |
| | Tetradecyl alcohol |
| | Pentadecyl alcohol |
| | Hexadecyl alcohol |
| | Heptadecyl alcohol |
| | Octadecyl alcohol |
| | Eicodecyl alcohol |
| | Docosyl alcohol, etc. |
| (Ester-1) Esters having 10 or more carbon atoms are effective. Examples of these esters include esters obtained by arbitrary combination of monovalent carboxylic acid having aliphatic and alicyclic or aromatic ring and monovalent alcohol having aliphatic and alicyclic or aromatic ring, esters obtained by arbitrary combination of polyvalent carboxylic acid | Ethyl caprylate |
| | Octyl caprylate |
| | Stearyl caprylate |
| | Myristyl caprate |
| | Docosyl caprate |
| | Cetyl caprate |
| | Stearyl caprate |
| | 2-Ethylhexyl laurate |
| | n-Decyl laurate |
| | 3-Methylbutyl myristate |
| | Cetyl myristate |
| | Stearyl myristate |
| | Isopropyl palmitate |
| | Neopentyl palmitate |

TABLE 4-continued

| Compound group | Name of compound |
| --- | --- |
| having aliphatic and alicyclic or aromatic ring and monovalent alcohol having aliphatic and alicyclic or aromatic ring, and esters obtained by arbitrary combination of monovalent carboxylic acid having aliphatic and alicyclic or aromatic ring and polyvalent alcohol having aliphatic and alicyclic or aromatic ring. | Nonyl palmitate |
| | Stearyl palmitate |
| | Cyclohexyl palmitate |
| | n-Butyl stearate |
| | 2-Methylbutyl stearate |
| | 3,5,5-Trimethylhexyl stearate |
| | n-Undecyl stearate |
| | Pentadecyl stearate |
| | Stearyl stearate |
| | Cyclohexylmethyl stearate |
| | Isopropyl behenate |
| | Hexyl behenate |
| | Lauryl behenate |
| | Behenyl behenate |
| | Cetyl benzoate |
| | Stearyl p-tert-butylbenzoate |
| | Dimyristyl phthalate |
| | Distearyl phthalate |
| | Dimyristyl oxalate |
| | Dicetyl oxalate |
| | Dicetyl malonate |
| | Dilauryl succinate |
| | Dilauryl glutarate |
| | Diundecyl adipate |
| | Dilauryl azelate |
| | Di-(n-nonyl) sebacate |

TABLE 5

| Compound group | Name of compound |
| --- | --- |
| (Ester-1) | Dineopentyl 1,18-octadecylmethylene-dicarboxylate |
| | Ethyleneglycol dimyristate |
| | Propyleneglycol dilaurate |
| | Propyleneglycol distearate |
| | Hexyleneglycol dipalmitate |
| | 1,5-Pentanediol distearate |
| | 1,2,6-Hexanetriol trimyristate |
| | 1,4-Cyclohexanediol didecyl |
| | 1,4-Cyclohexanedimethanol dimyristate |
| | Xylene glycol dicaprinate |
| | Xylene glycol distearate, etc. |
| (Ester-2) Also effective are ester of saturated aliphatic acid with branched aliphatic alcohol and ester of unsaturated aliphatic acid or saturated aliphatic acid which is branched or has substituents with aliphatic alcohol which is branched or has 16 or more carbon atoms. | 2-Ethylhexyl butyrate |
| | 2-Methylbutyl caproate |
| | 1-Ethylpentyl caproate |
| | 2-Methylpentyl caproate |
| | 2-Methylbutyl caprate |
| | 2-Methylpentyl caprate |
| | 2-Methylbutyl caprate |
| | 2-Ethylhexyl caprate |
| | 1-Methylpentyl caprate |
| | 2-Methylpentyl caprate |
| | 1,1-Dimethylpropyl laurate |
| | 2-Methylpentyl laurate |
| | 1-Ethylhexyl laurate |
| | 3,5,5-Trimethylhexyl laurate |
| | 3,7-Dimethyloctyl laurate |
| | 1-Ethylhexyl myristate |
| | 2-Ethylhexyl myristate |
| | 3,7-Dimethyloctyl myristate |
| | 1-Ethylpropyl palmitate |
| | 1-Ethylpentyl palmitate |
| | 2-Methylhexyl palmitate |
| | 2-Ethylhexyl palmitate |
| | 1-Ethylhexyl palmitate |
| | 3,5,5-trimethylhexyl palmitate |
| | 3,7-Dimethyloctyl palmitate |
| | 1-Methylpropyl stearate |
| | 1-Ethylpropyl stearate |
| | 2-Methylbutyl stearate |
| | 3-Methylbutyl stearate |
| | Neopentyl stearate |
| | 1-Methylhexyl stearate |
| | 2-Methylhexyl stearate |

TABLE 5-continued

| Compound group | Name of compound |
|---|---|
| | 3,5,5-Trimethylhexyl stearate |
| | 1-Methylheptyl stearate |
| | 1-Methyloctyl stearate |
| | 3,7-Dimethyloctyl stearate |
| | 1-Ethylpropyl behenate |
| | 2-Methylbutyl behenate |
| | 3,7-Dimethyloctyl behenate |
| | 1-Ethylpropyl behenate |
| | 2-Methylbutyl behenate |
| | 3-Methylbutyl behenate |
| | 2-Methylhexyl behenate |
| | 2-Ethylhexyl behenate |
| | 1-Methylheptyl behenate |
| | 3,7-Dimethyloctyl behenate |

TABLE 6

| Compound group | Name of compound |
|---|---|
| (Ester-2) | Stearyl oleate |
| | Behenyl oleate |
| | Stearyl linoleate |
| | Behenyl linoleate |
| | 3,7-Dimethyloctyl erucate |
| | Stearyl erucate |
| | Isostearyl erucate |
| | Cetyl isostearate |
| | Stearyl isostearate |
| | 2-Metylpentyl 12-hydroxystearate |
| | 2-Ethylhexyl 18-bromostearate |
| | Isostearyl 2-ketomyristate |
| | 2-Ethylhexyl 2-fluoromyristate, etc. |
| (Ester-3) | Cetyl butyrate |
| The use of esters having ΔT value (melting point-cloudy point) of not higher than 3° C. | Stearyl butyrate |
| | Behenyl butyrate |
| | 2-Methylbutyl caproate |

TABLE 6-continued

| Compound group | Name of compound |
|---|---|
| such as those disclosed in above cited JP-B-1-2398 among the foregoing esters makes it possible to exhibit thermochromic characteristics having a small hysteresis (width: 0.5 C. to 2.0° C.) on color density-temperature curve and a high responce. Examples of the esters having ΔT width of not greater than 3° C. include alkylester, arylester, arylakylester, alicyclic alkylester and branched ester of aromatic and aliphatic carboxylic acids, and substituted derivatives thereof. | 2-Methylpentyl caproate |
| | 1-Ethylpentyl caproate |
| | 2-Methylbutyl caprylate |
| | 2-Methylpentyl caprylate |
| | 2-Methylbutyl caprate |
| | 1-Methylpentyl caprate |
| | 2-Methylpentyl caprate |
| | 2-Ethylhexyl caprate |
| | 1,1-Dimethylpropyl laurate |
| | 2-Methylpentyl laurate |
| | 1-Ethylhexyl laurate |
| | 3,5,5-Trimethylhexyl laurate |
| | 3,7-Dimethyloctyl laurate |
| | 1-Ethylhexyl myristate |
| | 2-Ethylhexyl myristate |
| | 3,5,5-Trimethylhexyl myristate |
| | 3,7-Dimethyloctyl myristate |
| | n-Butyl palmitate |
| | 1-Ethylpropyl palmitate |
| | 1-Ethylpentyl palmitate |
| | 1-Ethylhexyl palmitate |
| | 3,5,5-Trimethylhexyl palmitate |
| | 3,7-Dimethyloctyl palmitate |
| | 1-Methylpropyl stearate |
| | 1-Ethylpropyl stearate |
| | n-Butyl stearate |
| | 3-Methylbutyl stearate |
| | n-Hexyl stearate |
| | 1-Methylhexyl stearate |
| | 2-Methylhexyl stearate |
| | 1-Methylheptyl stearate |
| | 1-Methyloctyl stearate |
| | 3,7-Dimethyloctyl stearate |
| | Lauryl stearate |
| | n-Butyl arachate |
| | n-Butyl behenate |
| | 1-Ethylpropyl behenate |

TABLE 7

| Compound group | Name of compound |
|---|---|
| (Ester-3) | 3-Methylbutyl behenate |
| | 2-Methylhexyl behenate |
| | 2-Ethylhexyl behenate |
| | 1-Methylheptyl behenate |
| | 3,7-Dimethyloctyl behenate |
| | n-Butyl erucate |
| | 3,7-Dimethyloctyl erucate |
| | Isostearyl erucate |
| | Stearyl isostearate |
| | Cetyl isostearate |
| | 2-Methylpentyl 12-hydroxystearate |
| | 2-Ethylhexyl 18-bromostearate |
| | Isostearate 2-ketomyristate |
| | 2-Ethylhexyl 2-fluoromyristate |
| | Stearyl oleate |
| | Behenyl oleate |
| | Stearyl linoleate |
| | Behenyl linoleate, etc. |
| (Ester-4) In order to provide a color memory thermochromism dependent on temperature change, i.e., discoloration with a great hysteresis (shape of curve made by plotting color density change with temperature change differs from change of temperature from low value to high value in discoloration temperature range to reversed change; the two curves make a loop) on color density-temperature curve, it is effective to use a carboxylic acid ester compound showing ΔT value (melting point-cloudy point) of not lower | Compound group (1) |
| | Stearyl 2-methylbenzoate |
| | Cetyl 4-tert-butylbenzoate |
| | Behenyl 4-cyclohexylbenzoate |
| | Myristyl 4-phenylbenzoate |
| | Lauryl 4-octylbenzoate |
| | Hexyl 3,5-dimethylbenzoate |
| | Stearyl 3-ethylbenzoate |
| | Decyl 4-isopropylbenzoate |
| | Stearyl 4-benzoylbenzoate |
| | Phenyl 4-tert-butylbenzoate |
| | 4-Chlorobenzyl 2-methylbenzoate |
| | Stearyl 4-chlorobenzoate |

TABLE 7-continued

| Compound group | Name of compound |
|---|---|
| than 5° C. to lower than 50° C. disclosed in JP-B-4-17154 proposed by the present applicant. | Myristyl 3-bromobenzoate |
| | Stearyl 2-chloro-4-bromobenzoate |
| Compound group (1) | Decyl 3,4-dichlorobenzoate |
| Carboxylic acid ester containing substituted aromatic group in molecule | Octyl 2,4-dibromobenzoate |
| | Cetyl 3-nitrobenzoate |
| Compound group (2) | Cyclohexylmethyl 4-aminobenzoate |
| Ester of carboxylic acid having unsubstituted aromatic ring and aromatic alcohol having 14 or more carbon atoms | Cetyl 4-diethylaminobenzoate |
| | Stearyl 4-anilinobenzoate |
| | Decyl 4-methoxybenzoate |
| Compound group (3) | Cetyl 4-methoxybenzoate |
| Carboxylic acid ester containing cycloalkyl group in molecule | Octyl 4-butoxybenzoate |
| | Cetyl 4-hydroxybenzoate |
| Compound group (4) | 4-Methoxyphenylmethyl benzoate |
| Ester of aliphatic acid having 6 or more carbon atoms with unsubstituted aromatic alcohol or phenol | Stearyl p-chlorophenylacetate |
| | Cetyl p-chlorophenylacetate |
| | Benzyl salicylate |
| Compound group (5) | Neopentyl salicylate |
| Ester of aliphatic acid having 4 or more carbon atoms with polarized aliphatic alcohol | 4-Methoxymethylphenylmethyl salicylate |
| | 4-Chlorophenylmethyl benzoate |
| | 4-Chlorophenylmethyl caprate |
| | 4-Methoxyphenylmethyl myristate |
| | 4-Methylphenylmethyl stearate |
| | 4-Nitrophenylmethyl stearate |

TABLE 8

| Compound group | Name of compound |
|---|---|
| (Ester-4; continued from above) | 4-Methylphenylmethyl caproate |
| | 2-Chlorophenylmethyl myristate |
| Compound group (6) | 4-Methoxyphenylmethyl caprate |
| Diester of dicarboxylic acid with aromatic alcohol or polarized aliphatic alcohol | 4-Chloropophenyl 11-bromolaurate |
| | 4-Isopropylphenyl stearate |
| | Compound group (2) |
| Compound group (7) | Stearyl 1-naphthoate |
| Other compounds | Cetyl benzilate |
| | Stearyl benzilate |
| | Decyl 3-benzoylpropionate |
| | Stearyl benzoate |
| | Cetyl benzoate |
| | Myristyl benzoate |
| | Compound group (3) |
| | Cyclohexylmethyl cinnamate |
| | Cyclohexyl laurate |
| | Cyclohexyl myristate |
| | Cyclohexyl palmitate |
| | Cyclohexylmethyl stearate |
| | Cyclohexylethyl stearate |
| | Stearyl cyclohexylethylacetate |
| | Stearyl 2-cyclohexylpropionate |
| | Stearyl cyclohexanecarboxylate |
| | Cyclohexyl 2-benzoylpropionate |
| | Compound group (4) |
| | Benzyl caproate |
| | Benzyl palmitate |
| | 3-Phenylpropyl stearate |
| | Phenyl 11-bromolaurate |
| | Compound group (5) |
| | Neopentyl octylate |
| | Neopentyl laurate |
| | Compound group (6) |
| | Dibenzyl sebacate |
| | Dineopentyl 4,4'-diphenylcarboxylate |
| | Dibenzyl azodicarboxylate |
| | Compound group (7) |
| | Benzyl cinnamate |
| | Heptyl stearate |
| | Didecyl adipate |
| | Dilauryl adipate |
| | Dimyristyl adipate |
| | Decetyl adipate |
| | Distearyl adipate |
| | Trilaurin |
| | Trimyristin |
| | Tristearin |
| | Dimyristin |
| | Distearin, etc. |

TABLE 9

| Compound group | Name of compound |
|---|---|
| (Ester-5) | n-Pentadecyl acetate |
| Also effective are aliphatic acid ester compound obtained from aliphatic monovalent alcohol having 9 or more odd number of carbon atoms and aliphatic carboxylic acid having even number of carbon atoms and aliphatic acid ester compound having from 17 to 23 carbon atoms obtained from n-pentyl alcohol or n-heptyl alcohol and aliphatic carboxylic acid having from 10 to 16 even number of carbon atoms. | n-Tridecyl butyrate |
| | n-Pentadecyl butyrate |
| | n-Undecyl caproate |
| | n-Tridecyl caproate |
| | n-Pentadecyl caproate |
| | n-Nonyl caprylate |
| | n-Undecyl caprylate |
| | n-Tridecyl caprylate |
| | n-Pentadecyl caprylate |
| | n-Heptyl caprylate |
| | n-Nonyl caprylate |
| | n-Undecyl caprylate |
| | n-Tridecyl caprylate |
| | n-Pentadecyl caprylate |
| | n-Pentyl laurate |
| | n-Heptyl laurate |
| | n-Nonyl laurate |
| | n-Undecyl laurate |
| | n-Tridecyl laurate |
| | n-Pentadecyl laurate |
| | n-Pentyl myristate |
| | n-Heptyl myristate |
| | n-Nonyl myristate |
| | n-Undecyl myristate |
| | n-Tridecyl myristate |
| | n-Pentadecyl myristate |
| | n-pentyl palmitate |
| | n-Heptyl palmitate |
| | n-Nonyl palmitate |
| | n-Undecyl palmitate |
| | n-Tridecyl palmitate |
| | n-Pentadecyl palmitate |
| | n-Nonyl stearate |

TABLE 9-continued

| Compound group | Name of compound |
|---|---|
| | n-Undecyl stearate |
| | n-Tridecyl stearate |
| | n-Pentadecyl stearate |
| | n-Nonyl eicosanate |
| | n-Undecyl eicosanate |
| | n-Tridecyl eicosanate |
| | n-Pentadecyl eicosanate |
| | n-Nonyl behenate |
| | n-Undecyl behenate |
| | n-Tridecyl behenate |
| | n-Pentadecl behenate, etc. |

TABLE 10

| Compound group | Name of compound |
|---|---|
| (Ketone-1) Aliphatic ketones having 10 or more carbon atoms | 2-Decanone, 3-Decanone, 4-Decanone, 2-Undecanone, 3-Undecanone, 4-Undecanone, 5-Undecanone, 2-Dodecanone, 3-Dodecanone, 4-Dodecanone, 5-Dodecanone, 2-Tridecanone, 3-Tridecanone, 2-Tetradecanone, 2-Pentadecanone, 8-Pentadecanone, 2-Hexadecanone, 3-Hexadecanone, 9-Heptadecanone, 2-Pentadecanone, 2-Octadecanone, 2-Nonadecanone, 10-Nonadecanone, 2-Eicosanone, 11-Eicosanone, 2-Heneicosanone, 2-Docosanone, Lauron, Stearon, etc. |
| (Ketone-2) Arylalkylketones having from 12 to 24 carbon atoms | n-Octadecanophenone, n-Heptadecanophenone, n-Hexadecanophenone, n-Pentadecanophenone, n-Tetradecanophenone, 4-n-Dodecaacetophenone, n-Tridecanophenone, 4-n-Undecanoacetopheflofle, n-Laurophenone, 4-n-Decanoacetophenone, n-Undecanophenone, 4-n-Nonylacetophenone, n-Decanophenone, 4-n-Octylacetophenone, n-Nonanophenone, n-Octanophenone, 4-n-Heptylacetophenone, 4-n-Hexylacetophenone, 4-Cyclohexylacetophenone, 4-Tert-butylpropiophenone, n-Heptaphenone, 4-n-Pentylacetophenone, Cyclohexyl phenyl ketone, Benzyl-n-butyl ketone, 4-n-Butyl acetophenone, n-Hexanophenone, 4-Isobutyl acetophenone, 1-Acetonaphthone, 2-Acetonaphthone, Cyclopentyl phenyl ketone, etc. |
| (Ethers) Aliphatic ethers having 10 or more carbon atoms | Dipentyl ether, Dihexyl ether, Diheptyl ether, Dioctyl ether, Dinonyl ether, Didecyl ether, Diundecyl ether, Didodecyl ether, Ditridecyl ether, Ditetradecyl ether, Dipentadecyl ether, Dihexadecyl ether, Dioctadecyl ether, Undecanediol dimethyl ether, Dodecanediol dimethyl ether, Tridecanediol dimethyl ether, Decanediol diethyl ether, Undecanediol diethyl ether, etc. |

As the electron accepting light-fastness providing agent which acts as the component (d) there is preferably used any of those listed in Tables 11 and 12.

TABLE 11

| Compound group | Name of compound |
|---|---|
| 1. Compound having aromatic ring free of substituents | 1,1-Bis(4-hydroxyphenyl)-n-hexane, 1,1-Bis(4-hydroxyphenyl)-2-ethylbutane, 1,1-Bis(4-hydroxyphenyl)-2-methylpentane, 1,1-Bis(4-hydroxyphenyl)-n-heptane, 1,1-Bis(4-hydroxyphenyl)-2,3-dimethylpentane, 1,1-Bis(4-hydroxyphenyl)-n-octane, 1,1-Bis(4-hydroxyphenyl)-2-ethylhexane, 1,1-Bis(4-hydroxyphenyl)-n-nonane, 1,1-Bis(4-hydroxyphenyl)-n-decane, 1,1-Bis(4-hydroxyphenyl)-3,7-dimethyloctane, 1,1-Bis(4-hydroxyphenyl)-n-undecane, 1,1-Bis(4-hydroxyphenyl)-n-dodecane, 1,1-Bis(4-hydroxyphenyl)-n-tridecane, 1,1-Bis(4-hydroxyphenyl)-n-tetradecane, |

TABLE 11-continued

| Compound group | Name of compound |
|---|---|
| | 1,1-Bis(4-hydroxyphenyl)-n-pentadecane, 1,1-Bis(4-hydroxyphenyl)-n-hexadecane, 1,1-Bis(4-hydroxyphenyl)-n-heptadecane, 1,1-Bis(4-hydroxyphenyl)-n-octadecane, etc. |
| 2. Compound having mono-substituted aromatic ring | 1,1-Bis(3-methyl-4-hydroxyphenyl)-n-hexane, 1,1-Bis(3-methyl-4-hydroxyphenyl)-2-ethylbutane, 1,1-Bis(3-methyl-4-hydroxyphenyl)-2-methylpentane, 1,1-Bis(3-methyl-4-hydroxyphenyl)-n-octane, 1,1-Bis(3-methyl-4-hydroxyphenyl)-2-ethylhexane, 1,1-Bis(3-methyl-4-hydroxyphenyl)-n-decane, 1,1-Bis(3-methyl-4-hydroxypheny1)-3,7-dimethyloctane, 1,1-Bis(3-methyl-4-hydroxyphenyl)-n-dodecane, 1,1-Bis(3-methyl-4-hydroxyphenyl)-n-tetradecane, |

TABLE 12

| Compound group | Name of compound |
|---|---|
| 2. Compound having mono-substituted aromatic ring (continued from above) | 1,1-Bis(3-methyl-4-hydroxyphenyl)-n-hexadecane, 1,1-Bis(3-methyl-4-hydroxyphenyl)-n-octadecane, etc. 1,1-Bis(3-methyl-4-hydroxyphenyl)-n-decane, 1,1-Bis(3-n-propyl-4-hydroxyphenyl)-n-decane, 1,1-Bis(3-isopropyl-4-hydroxyphenyl)-n-decane, 1,1-Bis(3-n-butyl-4-hydroxyphenyl)-n-decane, 1,1-Bis(3-sec-butyl-4-hydroxyphenyl)-n-decane, 1,1-Bis(3-isobutyl-4-hydroxyphenyl)-n-decane, 1,1-Bis(3-tert-butyl-4-hydroxyphenyl)-n-decane, 1,1-Bis(3-fluoro-4-hydroxyphenyl)-n-decane, 1,1-Bis(3-chloro-4-hydroxyphenyl)-n-decane, 1,1-Bis(3-bromo-4-hydroxyphenyl)-n-decane, 1,1-Bis(3-iodo-4-hydroxyphenyl)-n-decane, 1,1-Bis(2-methyl-4-hydroxyphenyl)-n-decane, 1,1-Bis(2-ethyl-4-hydroxyphenyl)-n-decane, 1,1-Bis(2-chloro-4-hydroxyphenyl)-n-decane, 1,1-Bis(2-bromo-4-hydroxyphenyl)-n-decane, etc. |
| 3. Compound having di-substituted aromatic ring | 1,1-Bis(2,3-dimethyl-4-hydroxyphenyl)-n-decane, 1,1-Bis(2-methyl-4-hydroxy-5-tert-butylphenyl)-n-decane, 1,1-Bis(2,6-dimethyl-4-hydroxyphenyl)-n-decane, 1,1-Bis(3,5-dimethyl-4-hydroxyphenyl)-n-decane, 1,1-Bis(3,5-di-sec-butyl-4-hydroxyphenyl)-n-decane, 1,1-Bis(3,5-di-tert-butyl-4-hydroxyphenyl)-n-decane, etc. |
| 4. Compound having tri-substituted aromatic ring | 1,1-Bis(2,3,5-trimethyl-4-hydroxyphenyl)-n-decane, 1,1-Bis(2,3,6-trimethyl-4-hydroxyphenyl)-n-decane, etc. |

As the light stabilizer which acts as the component (e) there is preferably used any of those listed in Tables 13 to 16.

TABLE 13

| Classification | Name of compound |
| --- | --- |
| Benzophenone-based ultraviolet absorber | 2,4-Dihydroxybenzophenone<br>2-Hydroxy-4-methoxybenzophenone<br>2,2'-Dihydroxy-4,4'-dimethoxybenzophenone<br>2,2',4,4'-Tetrahydroxybenzophenone<br>2-Hydroxy-4-methoxybenzophenone-5-sulfonic acid<br>2-Hydroxy-4-n-octyloxybenzophenone<br>Bis-(2-methoxy-4-hydroxy-5-benzoylphenyl)-methane<br>2-(2'-Hydroxy-3'–5'-di-t-amylphenyl)-benzophenone<br>2-Hydroxy-4-octadecyloxybenzophenone<br>2-Hydroxy-4-n-dodecyloxybenzophcnone<br>2,2'-Dihydroxy-4-methoxybenzophenone<br>2-Hydroxy-4-benzyloxybenzophenone, etc. |
| Salicyclic acid-based ultraviolet absorber | 2-4-Di-t-butylphenyl-3,5-di-t-butyl-4-hydroxybenzoate<br>Phenyl salicylate<br>4-t-Butylphenyl salicylate<br>4-t-Octylphenyl salicylate<br>Resorcinol monobenzoate, etc. |
| Cyano acrylate-based ultraviolet absorber | Ethyl-2-cyano-3,3-diphenyl acrylate<br>2-Ethylhexyl-2-cyano-3,3-diphenyl acrylate<br>2-Ethylhexyl-2-cyano-3-phenylcinnate, etc. |
| Benzotriazole-based ultraviolet absorber | 2-(5-t-Butyl-2-hydroxyphenyl)-benzotriazole<br>2-(5-Methyl-2-hydroxyphenyl)-benzotriazole<br>2-[2-Hydroxy-3,5-bis(a,a-dimethylbenzyl)phenyl]-2H-benzotriazole<br>2-(3,5-Di-t-butyl-2-hydroxyphenyl)-benzotriazole<br>2-(3-t-Butyl-5-methyl-2-hydroxphenyl)-benzotriazole<br>2-(3-Di-t-butyl-2-hydroxyphenyl)-5-chlorobenzotriazole<br>2-(3,5-Di-t-amyl-2-hydroxyphenyl)-benzotriazole<br>Condensate of methyl-3-[3-t-butyl-5-(2H-benzotriazole-2-yl)-4-hydroxyphenyl) propionate with polyethylene glycol having a molecular weight of 300<br>2-(3-Dodecyl-5-methyl-2-hydroxyphenyl)-benzottriazole<br>Condensate of methyl-3-[3-(2H-benzotriazole-2-yl)-5-t-butyl-4 hydroxyphenyl)propionate with polyethylene glycol having a molecular weight of 300<br>2-(3-t-Butyl-5-propyloxycarbonylethyl-2-hydroxyphenyl)-5-chlorobenzotriazole<br>2-[2-Hydroxyphenyl-3,5-di-(1,1'-dimethylbenzyl)phenyl]-2H-benzotriazole<br>2-(2-Hydroxy-5-t-octylphenyl)-2H-benzotriazole<br>2-(3-t-Butyl-5-octyloxycarbonylethyl)-2-hydroxyphenyl)-benzotriazole<br>2-(2-Hydroxy-4-octloxy-phenyl)-2H-benzotriazole |

TABLE 14

| Classification | Name of compound |
| --- | --- |
|  | 2-[2'-Hydroxy-3'-(3',4',5',6'-tetrahydrophthalimidemethyl)-5'-methylphenyl]-benzotriazole<br>2-(2-Hydroxy-5-t-butylphenyl)-benzotriazole, etc. |
| Oxalic acid anilide-based ultraviolet absorber | Ethanediamide-N-(2-ethoxyphenyl)-N'-(4-isododecylphenyl)<br>2,2,4,4-Tetramethyl-20-([62 -lauryloxycarbonyl)-ethyl-7-oxa-3,2O-diazadispiro[5,1,11,2)heneicosan-21-one, etc. |
| Hindered amine-based oxidative inhibitor | Dimethyl[1-(2-hydroxyethyl)-4-hydroxy-2,2,6,6-tetramethylpiperidine]succinate polycondensate<br>Poly[(6-(1,1,3,3-tetramethylbutyl)imino-1,3,5-triazine-2,4-diyl)((2,2,6,6-tetramethyl-4-piperidyl) imino)hexamethylene ((2,2,6,6-tetramethyl-4-piperidyl)imino)]<br>2-(3,5-Di-t-butyl-4-hydroxybenzyl)-2-n-butylmalonic acid bis(1,2,2,6,6-pentamethyl-4-piperidyl)<br>N,N'-bis(3-aminopropyl)ethylenediamine-2,4-bis]N-butyl-N-(1,2,2,6,6-pentamethyl-4-piperidyl)amino]-6-chloro-1,3,5-triazine condensate<br>Bis(1,2,2,6,6-pentamethyl-4-piperidyl) sebacate<br>4-Benzoyloxy-2,2,6,6-tetramethylpiperidine<br>Bis(2,2,6,6-tetramethyl-4-piperidyl) sebacate<br>1-[2-(3-(3 ,5-Di-t-butyl-4-hydroxyphenyl)propionyloxy)ethyl]-4-(3-(3,5-di-t-butyl-4-hydroxyphenyl)propionyloxy)-2,2,6,8-tetramethylpiperidine<br>8-Acetyl-3-dodecyl-7,7,9,9-tetramethyl-1,3,8-triazaspiro(4,5)decane-2,4-dione, etc. |
| Phenol-based oxidative inhibitor | 2,6-Di-t-butyl-4-methylphenol<br>Mixture of 2-t-butyl-4-methoxyphenol and 3-t-butyl-4- |

TABLE 14-continued

| Classification | Name of compound |
| --- | --- |
| | methoxyphenol |
| | 2,6-Di-t-butyl-4-ethylphenol |
| | Octadecyl-3-(3,5-di-t-butyl-4-hydroxyphenyl)propionate |
| | 2,2-Methylenebis(4-methyl-6-t-butylphenol) |
| | 4,4-Thiobis(3-methyl-6-t-butylphenol) |
| | 2,2-Thiobis(4-methyl-6-t-butylphenol) |
| | 4,4-butylidenebis(3-methyl-6-t-butylphenol) |
| | 3,9-Bis[1,1-dimethyl-2-(β-(3-t-butyl--4-hydroxy-5-methylphenyl)propionyloxy)ethyl-4,4,8,10-tetraoxaspiro(5,5)undecane |
| | 1,1,3-Tris(2-methyl-4-hydroxy-5-t-butylphenyl)butane |
| | 1,3,5-Trimethyl-2,4,6-tris(3,5-di-t-butyl-4-hydroxybenzyl)benzene |
| | Tetrakis[methylene-3-(3',5'-di-t-hydroxyphenyl)propionate]-methane |
| | 2,2-Ethylenebis(4,6-di-t-butylphenol) |
| | Bis[3,3'-bis-(4'-hydroxy-3'-t-butylphenyl)butyric acid]glycol ester |
| | 1,3,5-Tris(3',5'-di-t-butyl-4'-hydroxybenzyl)-S-triazine-2,4,6-(1H,3H,5H)trione |

TABLE 15

| Classification | Name of compound |
| --- | --- |
| | Tocophenol |
| | 1,3,5-Tris(4-t-butyl-3-hydroxy-2,6-dimethylbenzyl)isocyanurate |
| | Pentaerythritoltetrakis(3-laurylthiopropionate) |
| | Triethylene glycol-bis[3-(3-t-butyl-5-methyl-4-hydroxyphenyl)propionate |
| | 1,6-Hexanediol-bis[3-(3,5-di-t-butyl-4-hydroxyphenyl)propionate |
| | 2,2-Thioethylenebis[3-(3,5-di-t-butyl-4-hydroxyphenyl)propionate |
| | N,N'-hexamethylenebis(3,5-di-t-butyl-4-hydroxy-hydroxycinnamide) |
| | Tris-(3,5-di-t-butyl-4-hydroxybenzyl) isocyanurate |
| | Polymerized 2,2,4-trimethyl-1,2-hydroquinone |
| | Styrenated phenol |
| | 2,5-Di-t-butyl hydroquinone |
| | 2,4-Bis-(n-octylthio)-6-(4-hydroxy-3,5-di-t-butylanilino)-1,3,5-triazine |
| | Octylated diphenylamine, etc. |
| Sulfur-based oxidative inhibitor | Dilauryl 3,3'-thiodipropionate |
| | Dimyristyl 3,3'-thiodipropionate |
| | Distearyl 3,3'-thiodipropionate |
| | Stearyl thiopropylamide, etc. |
| Phosphoric acid-based oxidative inhibitor | Tris(2,4-di-t-butylphenyl)phosphite |
| | Bis(2,4-di-t-butylphenyl)pentaerythritol diphosphite |
| | 3,5-Di-t-butyl-4-hydroxy-benzyl phosphonate-diethylester |
| | Triphenyl phosphite |
| | Diphenyl isodecyl phosphite |
| | Phenyl diisodecyl phosphite |
| | 4,4'-Butylidene-bis(3-methyl-6-t-butylphenylditridecyl)phosphite |
| | Octadecyl phosphite |
| | Tris(nonylphenyl)phosphite |
| | 9,10-Dihydro-9-oxa-10-phosphenanethrene-10-oxide |
| | 10-(3,5-di-t-butyl-4-hydroxybenzyl)-9,10-dihydro-9-oxa-10-phosphophenanethrene-10-oxide |
| | 10-Decyloxy-9,10-dihydro-9-oxa-10-phosphaphenanethrene |
| | Cyclic neopentatetraylbis(2,4-di-t-butylphenyl)phosphite |
| | Cyclic neopentatetraylbis(2,6'-di-t-butyl-4-methylphenyl)phosphite |
| | 2,2-Methylenebis(4,6-di-t-butylphenyl)octyl phosphite, etc. |
| Singlet oxidative quenching agent | 1,4-Diazacyclo(2,2,2)octane |
| | n-Carotene |
| | 1,3-Cyclohexadiene |
| | 2-Diethylaminomethylfuran |
| | 2-Phenylaminometylfuran |
| | 9-Diethylaminomethylanthracene |

TABLE 16

| Classification | Name of compound |
|---|---|
| Singlet oxidative quenching agent | 5-Diethylaminomethyl-6-phenyl-3,4-dihydroxypyrane<br>Nickel dimethyl thiocarbamate<br>Nickel dibutyl thiocarbamate<br>Nickel-3,5-di-t-butyl-4-hydroxybenzyl-phosphoric acid monoethylate<br>Nickel-3,5-di-t-butyl-4-hydroxybenzyl-phosphoric acid monobutylate<br>Nickel[2,2-di-thiobis(4-t-octylphenolate)]-(n-butylamine)<br>Nickel[2,2-di-thiobis(4-t-octylphenolate)]-(2-ethylhexylamine)<br>Nickelbis[2,2'-thiobis(4-t-octylphenolate)]<br>Nickelbis[2,2'-sulfon(4-t-octylphenolate)]<br>Nickelbis(2-hydroxy-5-methoxyphenyl-N-n-butylaldoimine<br>Nickelbis(dithiobenzyl)<br>Nickelbis(dithioacetyl), etc. |
| Super oxide anion quenching agent | Complex of super oxide dismutase with cobalt and nickel |
| Ozone quenching agent | 4,4'-Thiobis(6-t-butyl(6-t-butyl-m-cresol)<br>2,4,6-Tri-t-butylphenol<br>1,4-Diazadicyclo(2,2,2)octane<br>N-phenyl-β-naphthylamine<br>α-Tocophenol<br>4,4'-Methylene-bis(2,6-di-t-butylphenol)<br>p,p'-Diaminodiphenylmethane<br>2,2'-Methylene-bis(6-t-butyl-P-cresol)<br>N,N'-diphenyl-p-phenylenediamine<br>N,N'-diphenylethylenediamine<br>N-isopropyl-N'-phenyl-p-phenylenediamine, etc. |
| Visible light absorber<br>* Dyes | C.I. Solvent Yellow 19, 21, 61<br>C.I. Solvent Orange 5, 6<br>C.I. Solvent Red 8, 24<br>C.I. Solvent Violet 14, 21<br>C.I. Solvent Blue 11, 25<br>C.l. Solvent Black 5, 125, etc. |
| Visible light absorber]<br>* Pigments | Color Index No.<br>10825    21205<br>11680    45170<br>11725    50440<br>11780    58055<br>12060    69800<br>12120    69810<br>12490    70600<br>12500    74160<br>12710    74265<br>21090    127755, etc.<br>21110<br>21165<br>21180 |

The metallic lust pigment to be incorporated in the layer of light stabilizer and/or metallic lust pigment layer (f) to be used in the invention is a pigment such as metallic luster pigment, transparent titanium dioxide, transparent iron oxide, transparent cesium oxide and transparent zinc oxide.

As the metallic lust pigment there may be used a metallic luster pigment having a particle size of from 5 to 100 $\mu$m having natural mica coated with titanium oxide or a metallic luster pigment having flat piece of glass coated with titanium oxide. Specific examples of these metallic luster pigments include metallic luster pigment having a particle size of from 5 $\mu$m to 60 $\mu$m having natural mica coated with from 41 to 44% by weight of titanium oxide, silver metallic luster pigment having a particle size of from 5 $\mu$m to 100 $\mu$m having natural mica coated with from 16 to 39% by weight of titanium oxide, metallic color luster pigment having natural mica coated with from 45 to 58% by weight of titanium oxide and coated with from 4 to 10% by weight of iron oxide, metallic color luster pigment having natural mica coated with from 45 to 58% by weight of titanium oxide and coated with from 0.5 to 10% by weight of non-thermochromic dyed pigment, and metallic luster pigment having an average thickness of from 1 $\mu$m to 10 $\mu$m and an average particle size of from 5 $\mu$m to 500 $\mu$m having flat piece of glass coated with titanium oxide.

These materials which block mainly ultraviolet rays can be incorporated in the composition in an amount of from 0.1 to 40 parts by weight based on 1 part by weight of the component (a). Alternatively, a layer containing these materials in an amount of from 0.1 to 40 parts by weight may be laminated or used with the thermochromic layer.

The present invention will be further described in the following examples and comparative examples.

Processes for the preparation of reversible thermochromic compositions 1 to 16 according to the invention and microcapsuled pigments comprising these compositions incorporated therein will be described hereinafter.

EXAMPLE 1

Preparation of Reversible Thermochromic Composition 1 and Microcapsuled Pigment Comprising Composition 1 Incorporated Therein 1.5 parts by weight of 1,2-benz-6-(N-ethyl-N-isobutylamino)fluoran, 6.0 parts by weight of 2,4-dihydroxy-4'-methylbenzophenone and 50.0 parts by weight of n-nonyl palmitate were mixed. The mixture was then heated to a temperature of 120° C. to melt. Thus, a reversible thermochromic composition 1 was obtained as a homogeneously compatibilized material. To the reversible thermochromic composition 1 were then added 30 parts by weight of an aromatic isocyanate prepolymer and 30 parts by weight of ethyl acetate as wall membrane-forming materials. The mixture was then heated to a temperature of 70° C. to make uniform dissolution. Thus, a mixed solution was prepared. The mixed solution was then stirred in 100 parts by weight of a 5% aqueous solution of gelatin so that it was microfinely emulsified. The emulsion was further stirred for 1 hour. The emulsion was then stirred for 5 hours while being kept at a temperature of 80° C. to obtain a raw solution of microcapsule. The raw solution was then subjected to centrifugal separation to obtain a microcapsuled pigment containing the reversible thermochromic composition 1 which becomes fully colorless at a temperature of not lower than 32° C. and is colored fully pink at a temperature of not higher than 15° C.

EXAMPLES 2–11
Preparation of Reversible Thermochromic Compositions 2 to 11 and Microcapsuled Pigments Comprising the Compositions 2 to 11 Incorporated Therein Reversible thermochromic compositions 2 to 11 and microcapsuled pigments comprising these compositions incorporated therein were obtained in the same manner as the reversible thermochromic composition 1 except that the combination of components (a), (b) and (c) was varied.

The formulation, color change and discoloration temperature of these reversible thermochromic compositions are set forth in Table 17.

The figure in parentheses in Table 17 indicate parts by weight.

Reversible thermochromic compositions 12 to 14 and microcapsuled pigments comprising these compositions incorporated therein were obtained in the same manner as the reversible thermochromic composition 2 except that to the components (a), (b) and (c) was added a component (d).

The formulation of these reversible thermochromic compositions are set forth in Table 18.

Since as the components (a), (b) and (c) there were used the same compounds as used for the reversible thermochromic composition 2, the parts by weight of these components used are set forth in Table 18.

TABLE 18

| Reversible thermochromic composition | Components (a), (b) and (c) as used for reversible thermochromic composition 2 | | | (d) Light-fastness providing agent | Color change/discoloration temperature ($T_1$, $T_4$) |
| --- | --- | --- | --- | --- | --- |
| | a | b | c | | |
| 12 | (1.5) | (2.0) | (50.0) | 1,1-Bis(4-hydroxyphenyl)-n-decane (4.0) | Pink←→colorless 15° C., 32° C. |
| 13 | (1.5) | (3.0) | (50.0) | 1,1-Bis(4-hydroxyphenyl)-n-decane (3.0) | Pink←→colorless 15° C., 32° C. |
| 14 | (1.5) | (4.0) | (50.0) | 1,1-Bis(4-hydroxyphenyl)-n-decane (2.0) | Pink←→colorless 15° C., 32° C. |

EXAMPLES 15–16
Preparation of Reversible Thermochromic Compositions 15 and 16 and Microcapsuled Pigments Comprising the Compositions 15 and 16 Incorporated Therein Reversible thermochromic compositions 15 and 16 and microcapsuled pigments comprising these compositions

TABLE 17

| Reversible thermochromic composition | a. Electron donating compound | b. Ultraviolet-absorbing electron accepting compound | c. Discoloration temperature adjustor | Color change/discoloration temperature ($T_1$, $T_4$) |
| --- | --- | --- | --- | --- |
| 1 | 1,2-Benz-6-(N-ethyl-N-isobutylamino)fluoran (1.5) | 2,4-Dihydroxy-4'-methylbenzophenone (6.0) | n-Nonyl palmitate (50.0) | Pink ←→ colorless 15° C., 32° C. |
| 2 | 1,2-Benz-6-(N-ethyl-N-isobutylamino)fluoran (1.5) | 2,4-Dihydroxy-4'-n-propylbenzophenone (6.0) | n-Nonyl palmitate (50.0) | Pink ←→ colorless 15° C., 32° C. |
| 3 | 1,2-Benz-6-(N-ethyl-N-isobutylamino)fluoran (1.5) | 2,4-Dihydroxy-4'-n-pentylbenzophenone (6.0) | n-Nonyl palmitate (50.0) | Pink ←→ colorless 15° C., 32° C. |
| 4 | 1,2-Benz-6-(N-ethyl-N-isobutylamino)fluoran (1.5) | 2,4-Dihydroxy-4'-n-heptylbenzophenone (6.0) | n-Nonyl palmitate (50.0) | Pink ←→ colorless 15° C., 32° C. |
| 5 | 1,2-Benz-6-(N-ethyl-N-isobutylamino)fluoran (1.5) | 2,4-Dihydroxy-4'-methoxybenzophenone (6.0) | n-Nonyl palmitate (50.0) | Pink ←→ colorless 15° C., 32° C. |
| 6 | 1,2-Benz-6-(N-ethyl-N-isobutylamino)fluoran (1.5) | 2,4-Dihydroxy-4'-n-propoxybenzophenone (6.0) | n-Nonyl palmitate (50.0) | Pink ←→ colorless 15° C., 32° C. |
| 7 | 1,2-Benz-6-(N-ethyl-N-isobutylamino)fluoran (1.5) | 2,4-Dihydroxy-4'-n-pentyloxybenzophenone (6.0) | n-Nonyl palmitate (50.0) | Pink ←→ colorless 15° C., 32° C. |
| 8 | 3-(2-Ethoxy-4-N-ethylanilinophenyl)-3-(1-ethyl-2-methyl indol-3-yl)-4-azaphthalide (1.5) | 2,4-Dihydroxy-4'-n-propylbenzophenone (6.0) | n-Nonyl palmitate (50.0) | Blue ←→ colorless 15° C., 32° C. |
| 9 | 2,6-Bis(2-butoxyphenyl)-4-(4-dimethyl aminophenyl)pyridine (1.5) | 2,4-Dihydroxy-4'-n-propylbenzophenone (6.0) | n-Nonyl palmitate (50.0) | Yellow ←→ colorless 15° C., 32° C. |
| 10 | 1,2Benz-6-(N-ethyl-N-isobutylamino)fluoran (1.5) | 2,4-Dihydroxy-4'-n-propylbenzophenone (6.0) | Stearyl laurate (50.0) | Pink ←→ colorless 37° C., 42° C. |
| 11 | 1,2-Benz-6-(N-ethyl-N-isobutylamino)fluoran (1.5) | 2,4-Dihydroxybenzophenone (6.0) | n-Butyl stearate (50.0) | Pink ←→ colorless 18° C., 22° C. |

EXAMPLES 12–14
Preparation of Reversible Thermochromic Compositions 12 to 14 and Microcapsuled Pigments Comprising the Compositions 12 to 14 Incorporated Therein incorporated therein were obtained in the same manner as the reversible thermochromic composition 2 except that to the components (a), (b) and (c) were added components (d) and (e).

The formulation of these reversible thermochromic compositions are set forth in Table 19.

Since as the components (a), (b) and (c) there were used the same compounds as used for the reversible thermochromic composition 2, the parts by weight of these components used are set forth in Table 19.

Preparation of Light-fastness Test Specimen 17

43.0 parts by weight of a microcapsuled pigment comprising the reversible thermochromic composition 2 of Example 2 made of the components (a), (b) and (c) were uniformly stirred in a vehicle containing 50.0 parts by weight of an ethylene-vinyl acetate copolymer resin emulsion, 3.0 parts by weight of an anti-foaming agent, 1.0 part by weight of a thickening agent (sodium alginate), 3.0

TABLE 19

| Reversible thermochromic composition | Components (a), (b) and (c) as used for reversible thermo-chromic composition 2 | | | (d) Light-fastness providing agent | (e) Light stabilizer | Color/discoloration temperature ($T_1$, $T_4$) |
|---|---|---|---|---|---|---|
| | a | b | c | | | |
| 15 | (1.5) | (3.0) | (50.0) | 1,1-Bis(4-hydroxyphenyl)-n-decane (3.0) | 2-(3-t-Butyl-5-methyl-2-hydroxyphenyl)-5-chlorobenzotriazole (0.5) 2-(3,5-Di-t-butyl-4-hydroxybenzyl)-2-n-butylmalonic acid bis(1,2,2,6,6-penta-methyl-4-piperidyl) (0.5) | Pink←→colorless 15° C., 32° C. |
| 16 | (1.5) | (2.0) | (50.0) | 1,1-Bis(4-hydroxyphenyl)-n-decane (4.0) | 2-(3-t-Butyl-5-methyl-2-hydroxyphenyl)-5-chlorobenzotriazole (1.5) 2-(3,5-Di-t-butyl-4-hydroxybenzyl)-2-n-butylmalonic acid bis(1,2,2,6,6-penta-methyl-4-piperidyl) (0.5) | Pink←→colorless 15° C., 32° C. |

Performance Test

In order to explain the effect of the reversible thermochromic compositions of Examples 1 to 16, light-fastness test specimens 1 to 16 obtained by forming a reversible thermochromic layer of microcapsuled pigments containing these compositions on a synthetic paper were subjected to performance test.

Preparation of Light-fastness Specimen 1

43.0 parts by weight of a microcapsuled pigment comprising the reversible thermochromic composition 1 of Example 1 incorporated therein were uniformly stirred in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent and 1.0 part by weight of a preservative to obtain a reversible thermochromic screen ink.

The foregoing reversible thermochromic screen ink was then screen-printed on a synthetic white paper to prepare a reversible thermochromic print as a light-fastness test specimen 1.

Preparation of Light-fastness Test Specimens 2–16

Light-fastness test specimens 2 to 16 were prepared from microcapsuled pigments comprising the reversible thermochromic compositions 2 to 16 of Examples 2 to 16 incorporated therein in the same manner as the light-fastness test specimen 1.

The process for the preparation of light-fastness test specimens 17 to 21 having a layer of a light stabilizer and/or metallic luster pigment (f) provided on a reversible thermochromic layer of microcapsuled pigments comprising the reversible thermochromic compositions 2, 13 and 15 incorporated therein formed on a synthetic paper, respectively, will be described hereinafter.

parts by weight of a leveling agent and 1.0 part by weight of a preservative to obtain a reversible thermochromic screen ink.

The foregoing reversible thermochromic screen ink was then screen-printed on a synthetic white paper to form a reversible thermochromic layer thereon. A screen ink obtained by uniformly stirring 5.0 parts by weight of 2-(3,5-di-t-amyl-2-hydroxyphenyl)benzotriazole as a light stabilizer in a vehicle consisting of 50 parts by weight of an acrylic resin solution (solid content: 50%; xylene: 50%), 45 parts by weight of cyclohexanone, 3.0 parts by weight of a leveling agent, 1.0 part by weight of an anti-foaming agent and 1.0 part by weight of a viscosity modifier was then printed on the reversible thermochromic layer to form a layer of a light stabilizer (f). Thus, a light-fastness test specimen 17 was prepared.

Preparation of Light-fastness Test Specimen 18

43.0 parts by weight of a microcapsuled pigment comprising the reversible thermochromic composition 13 of Example 13 made of the components (a), (b), (c), and (d) were uniformly stirred in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent and 1.0 part by weight of a preservative to obtain a reversible thermochromic screen ink.

The foregoing reversible thermochromic screen ink was then screen-printed on a synthetic white paper to form a reversible thermochromic layer thereon. A screen ink obtained by uniformly stirring 5.0 parts by weight of 2-(3, 5-di-t-amyl-2-hydroxyphenyl)benzotriazole as a light stabilizer in a vehicle consisting of 50 parts by weight of an acrylic resin solution (solid content: 50%; xylene: 50%), 45 parts by weight of cyclohexanone, 3.0 parts by weight of a leveling agent, 1.0 part by weight of an anti-foaming agent and 1.0 part by weight of a viscosity modifier was then printed on the reversible thermochromic layer to form a layer of a light stabilizer (f). Thus, a light-fastness test specimen 18 was prepared.

Preparation of Light-fastness Test Specimen 19

43.0 parts by weight of a microcapsuled pigment comprising the reversible thermochromic composition 15 of Example 15 made of the components (a), (b), (c), (d) and (e) were uniformly stirred in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent and 1.0 part by weight of a preservative to obtain a reversible thermochromic screen ink.

The foregoing reversible thermochromic screen ink was then screen-printed on a synthetic white paper to form a reversible thermochromic layer thereon. A screen ink obtained by uniformly stirring 5.0 parts by weight of 2-(3, 5-di-t-amyl-2-hydroxyphenyl)benzotriazole as a light stabilizer in a vehicle consisting of 50 parts by weight of an acrylic resin solution (solid content: 50%; xylene: 50%), 45 parts by weight of cyclohexanone, 3.0 parts by weight of a leveling agent, 1.0 part by weight of an anti-foaming agent and 1.0 part by weight of a viscosity modifier was then printed on the reversible thermochromic layer to form a layer of a light stabilizer (f). Thus, a light-fastness test specimen 19 was prepared.

Preparation of Light-fastness Test Specimen 20

43.0 parts by weight of a microcapsuled pigment comprising the reversible thermochromic composition 15 of Example 15 made of the components (a), (b), (c), (d) and (e) were uniformly stirred in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent and 1.0 part by weight of a preservative to obtain a reversible thermochromic screen ink.

The foregoing reversible thermochromic screen ink was then screen-printed on a synthetic white paper to form a reversible thermochromic layer thereon. A screen ink obtained by uniformly stirring 1.5 parts by weight of a metallic luster pigment (trade name: Iriodin 219, produced by Merck Japan Ltd.) in a vehicle consisting of 45 parts by weight of cyclohexanone, 3.0 parts by weight of a leveling agent, 1.0 part by weight of an anti-foaming agent and 1.0 part by weight of a viscosity modifier was then printed on the reversible thermochromic layer to form a layer of a metallic luster pigment (f). Thus, a light-fastness test specimen 20 was prepared.

Preparation of Light-fastness Test Specimen 21

43.0 parts by weight of a microcapsuled pigment comprising the reversible thermochromic composition 15 of Example 15 made of the components (a), (b), (c), (d) and (e) were uniformly stirred in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent and 1.0 part by weight of a preservative to obtain a reversible thermochromic screen ink.

The foregoing reversible thermochromic screen ink was then screen-printed on a synthetic white paper to form a reversible thermochromic layer thereon. A screen ink obtained by uniformly stirring 1.5 parts by weight of a metallic luster pigment (trade name: Iriodin 219, produced by Merck Japan Ltd.) and 5.0 parts by weight of 2-(3,5-di-t-amyl-2-hydroxyphenyl)benzotriazole as a light stabilizer in a vehicle consisting of 50 parts by weight an acrylic resin solution (solid content: 50%; xylene] 50%), 45 parts by weight of cyclohexanone, 3.0 parts by weight of a leveling agent, 1.0 part by weight of an anti-foaming agent and 1.0 part by weight of a viscosity modifier was then printed on the reversible thermochromic layer to form a layer of a light stabilizer and a metallic luster pigment (f). Thus, a light-fastness test specimen 21 was prepared.

COMPARATIVE EXAMPLES 1–5

The process for the preparation of reversible thermochromic compositions 17 to 21 of Comparative Examples 1 to 5 to be used in Comparative Examples 1 to 5, respectively, and microcapsuled pigments comprising the compositions incorporated therein will be described hereinafter.

Preparation of Reversible Thermochromic Composition 17 of Comparative Example 1 and Microcapsuled Pigment Comprising the Composition 17 Incorporated Therein 1.5 parts by weight of 1,2-benz-6-(N-ethyl-N-isobutylamino)fluoran, 6.0 parts by weight of 2,4-bis(4-dihydroxyphenyl) and 50.0 parts by weight of n-nonyl palmitate were mixed. The mixture was then heated to a temperature of 120° C. to melt. Thus, a reversible thermochromic composition 17 was obtained as a homogeneously compatibilized material. To the reversible thermochromic composition 17 were then added 30 parts by weight of an aromatic isocyanate prepolymer and 30 parts by weight of ethyl acetate as wall membrane-forming materials. The mixture was then heated to a temperature of 70° C. to make uniform dissolution. Thus, a mixed solution was prepared. The mixed solution was then stirred in 100 parts by weight of a 5% aqueous solution of gelatin so that it was microfinely emulsified. The emulsion was further stirred for 1 hour. The emulsion was then stirred for 5 hours while being kept at a temperature of 80° C. to obtain a raw solution of microcapsule. The raw solution was then subjected to centrifugal separation to obtain a microcapsuled pigment containing the reversible thermochromic composition 17 which becomes fully colorless at a temperature of not lower than 32° C. and is colored fully pink at a temperature of not higher than 15° C.

Preparation of Reversible Thermochromic Compositions 18 to 21 of Comparative Examples 2 to 5 and Microcapsuled Pigments Comprising the Composition 18 to 21 Incorporated Therein Reversible thermochromic compositions 18 and 19 of Comparative Examples 2 and 3 and microcapsuled pigments comprising the compositions 18 and 19 incorporated therein were obtained in the same manner as the reversible thermochromic composition 17 except that the various components were changed.

Reversible thermochromic compositions 20 and 21 and microcapsuled pigments comprising the compositions 20 and 21 incorporated therein were obtained in the same manner as the reversible thermochromic composition 17 of Comparative Example 1 except that to the various components used was added a component (e).

The formulation of the reversible thermochromic compositions 17 to 21 of Comparative Examples 1 to 5 are set forth in Table 20.

The symbol "B" in the constituents in Table 20 indicates a conventional electron accepting compound.

TABLE 20

| Reversible thermochromic composition | a. Electron donating compound | B. Electron accepting compound | c. Discoloration temperature adjustor | e. Light stabilizer | Color change/ discoloration temperature ($T_1$, $T_4$) |
|---|---|---|---|---|---|
| 17 | 1,2-Benz-6-(N-ethyl-isobutylamino)fluoran (1.5) | 2,2-Bis(4-hydroxyphenyl)propane (6.0) | n-Nonyl palmitate (50.0) | | Pink ←→ colorless 15° C., 32° C. |
| 18 | 3-(2-Ethoxy-4-N-ethylanilinophenyl)-3-(1-ethyl-2-methylindol-3-yl)-4-azaphthalide (1.5) | 2,2-Bis(4-hydroxyphenyl)propane (6.0) | n-Nonyl palmitate (50.0) | | Blue ←→ colorless 15° C., 32° C. |
| 19 | 2,6-Bis(2-butoxyphenyl)-4-(4-dimethylaminophenyl)-pyridine (1.5) | 2,2-Bis(4-hydroxyphenyl)hexafluoro propane (6.0) | n-Nonyl palmitate (50.0) | | Yellow ←→ colorless 15° C., 32° C. |
| 20 | 1,2-Benz-6-(N-ethyl-N-isobutylamino(fluroan (1.5) | 2,2-Bis(4-hydroxypenyl)propane (6.0) | n-Nonyl palmitate (50.0) | 2-(5-t-Butyl-2-hydroxyphenyl)benzo triazole (1.0) | Pink ←→ colorless 15° C., 32° C. |
| 21 | 1,2-Benz-6-(N-ethyl-N-isobutylamino)fluoran (1.5) | 2,2-Bis(4-hydroxyphenyl)propane (6.0) | n-Nonyl palmitate (50.0) | 2-(5-t-Butyl-2-hydroxyphenyl)benzo triazole (5.0) | Pink ←→ coloreless 12° C., 32° C. |

The preparation of comparative light-fastness test specimens 22 to 26 having a reversible thermochromic layer of microcapsuled pigments containing the foregoing comparative reversible thermochromic compositions 17 to 21 formed on a synthetic paper, respectively, will be described hereinafter.

Preparation of Comparative Light-fastness Test Specimen 22

43.0 parts by weight of a microcapsuled pigment comprising the reversible thermochromic composition 17 of Comparative Example 1 incorporated therein were uniformly stirred in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent and 1.0 part by weight of a preservative to obtain a reversible thermochromic screen ink.

The foregoing reversible thermochromic screen ink was then screen-printed on a synthetic white paper to prepare a reversible thermochromic print having a reversible thermochromic layer formed thereon as a light-fastness test specimen 22.

Preparation of Comparative Light-fastness Test Specimens 23–26

Light-fastness test specimens 23 to 26 were prepared in the same manner as the light-fastness test specimen 22 except that microcapsuled pigments having the reversible thermochromic compositions 18 to 21 of Comparative Examples 2 to 5 incorporated therein were prepared, respectively.

Testing Method for Light-fastness in Quenched State

Using a Type SUNTEST CPS xenon arc lamp testing machine (produced by Herennius Inc. of Germany), test specimens 1 to 21 comprising reversible thermochromic compositions of the invention and test specimens 22 to 26 comprising comparative reversible thermochromic compositions were examined for light-fastness in quenched state.

For the light-fastness test, the radiant intensity of the xenon arc lamp was adjusted to 70,000 lux, and the distance between the light source and the test specimen was predetermined to 21 cm.

For the test, the test specimens 1 to 16 and the test specimens 22 to 26 were each irradiated with light from the xenon arc lamp on four points on the surface thereof for 5 hours, 10 hours, 15 hours and 20 hours.

The test specimens 17 to 21 were each irradiated with light from the xenon arc lamp on four points on the surface thereof for 10 hours, 20 hours, 30 hours and 40 hours.

Results of Light-fastness Test

Table 21 shows the results of light-fastness test in quenched state on the test specimens 1 to 11 comprising the reversible thermochromic compositions of Examples 1 to 11 made of the components (a), (b) and (c) of the invention.

The term "composition" as used in Table 21 indicates the reversible thermochromic composition incorporated in the test specimen. The term "constituent element" as used in Table 21 indicates various components (a) to (e) incorporated in the composition and the layer (f) of light stabilizer and/or metallic luster pigment provided on the thermochromic layer.

TABLE 21

| Test specimen | Composition | Constituent element | Unirradiated | 5 hours | 10 hours | 15 hours | 20 hours |
|---|---|---|---|---|---|---|---|
| 1 | Reversible thermochromic composition 1 | a, b, c | 100% | 94% | 76% | 63% | 43% |
| 2 | Reversible thermochromic composition 2 | a, b, c | 100% | 97% | 81% | 65% | 45% |
| 3 | Reversible thermochromic composition 3 | a, b, c | 100% | 98% | 85% | 70% | 51% |
| 4 | Reversible thermochromic composition 4 | a, b, c | 100% | 98% | 86% | 69% | 50% |
| 5 | Reversible thermochromic composition 5 | a, b , c | 100% | 93% | 74% | 62% | 42% |
| 6 | Reversible thermochromic composition 6 | a, b, c | 100% | 96% | 79% | 64% | 43% |
| 7 | Reversible thermochromic composition 7 | a, b, c | 100% | 97% | 82% | 67% | 50% |
| 8 | Reversible thermochromic composition 8 | a, b, c | 100% | 99% | 95% | 89% | 74% |
| 9 | Reversible thermochromic composition 9 | a, b, c | 100% | 89% | 78% | 62% | 45% |
| 10 | Reversible thermochromic composition 10 | a, b, c | 100% | 97% | 82% | 67% | 46% |

TABLE 21-continued

| Test specimen | Composition | Constituent element | Unirradiated | 5 hours | 10 hours | 15 hours | 20 hours |
|---|---|---|---|---|---|---|---|
| 11 | Reversible thermochromic composition 11 | a, b, c | 100% | 90% | 69% | 55% | 38% |

Table 22 shows the results of light-fastness test in quenched state on the test specimens 12 to 14 comprising the reversible thermochromic compositions of Examples 12 to 14 made of the components (a), (b), (c) and (d) of the invention.

TABLE 22

| Test specimen | Composition | Constituent element | Unirradiated | 5 hours | 10 hours | 15 hours | 20 hours |
|---|---|---|---|---|---|---|---|
| 12 | Reversible thermochromic composition 12 | a, b, c, d | 100% | 100% | 99% | 96% | 92% |
| 13 | Reversible thermochromic composition 13 | a, b, c, d | 100% | 100% | 98% | 95% | 90% |
| 14 | Reversible thermochromic composition 14 | a, b, c, d | 100% | 100% | 97% | 93% | 88% |

Table 23 shows the results of light-fastness test in quenched state on the test specimens 15 and 16 comprising the reversible thermochromic compositions of Examples 15 and 16 made of the components (a), (b), (c), (d) and (e) of the invention.

TABLE 23

| Test specimen | Composition | Constituent element | Unirradiated | 5 hours | 10 hours | 15 hours | 20 hours |
|---|---|---|---|---|---|---|---|
| 15 | Reversible thermochromic composition 15 | a, b, c, d, e | 100% | 100% | 100% | 98% | 94% |
| 16 | Reversible thermochromic composition 16 | a, b, c, d, e | 100% | 100% | 100% | 99% | 96% |

Table 24 shows the results of light-fastness test in quenched state on the test specimens 17 to 21 having a layer of light stabilizer and/or metallic lust pigment (f) provided on the reversible thermochromic layer formed by the reversible thermochromic compositions of Examples 2, 13 and 15 of the invention.

TABLE 24

| Test specimen | Composition | Constituent element | Unirradiated | 10 hours | 20 hours | 30 hours | 40 hours |
|---|---|---|---|---|---|---|---|
| 17 | Reversible thermochromic composition 2 | a, b, c, f (layer of light stabilizer) | 100% | 100% | 99% | 89% | 69% |
| 18 | Reversible thermochromic composition 13 | a, b, c, d f (layer of light stabilizer) | 100% | 100% | 100% | 96% | 87% |
| 19 | Reversible thermochromic composition 15 | a, b, c, d, e, f (layer of light stabilizer) | 100% | 100% | 100% | 97% | 91% |
| 20 | Reversible thermochromic composition 15 | a, b, c, d, e, f (layer of metallic luster pigment) | 100% | 100% | 100 | 99% | 95% |
| 21 | Reversible thermochromic composition 15 | a, b, c, d, e f (layer of light stabilizer and metallic luster pigment) | 100% | 100% | 100% | 100% | 99% |

Table 25 shows the results of light-fastness test in quenched state on the test specimens 22 to 26 comprising the reversible thermochromic compositions 17 to 21 of Comparative Examples 1 to 5.

TABLE 25

| Test specimen | Composition | Constituent element | Unirradiated | 5 hours | 10 hours | 15 hours | 20 hours |
|---|---|---|---|---|---|---|---|
| 22 | Reversible thermochromic composition 17 | a, B, c | 100% | 72% | 40% | 30% | 16% |
| 23 | Reversible thermochromic composition 18 | a, B, c | 100% | 52% | 15% | 10% | 7% |
| 24 | Reversible thermochromic composition 19 | a, B, c | 100% | 68% | 35% | 21% | 12% |
| 25 | Reversible thermochromic composition 20 | a, B, c, e | 100% | 89% | 53% | 35% | 24% |
| 26 | Reversible thermochromic composition 21 | a, B, c, e | 100% | 95% | 80% | 65% | 46% |

As can be seen in the foregoing results of light-fastness test in quenched state, the reversible thermochromic compositions 1 to 16 comprising the components (a), (b) and (c) of the invention are remarkably excellent in light-fastness as compared with the reversible thermochromic compositions 17 to 21 comprising conventional components (a), B and (c).

Further, the addition of the component (d) to the reversible thermochromic composition comprising the components (a), (b) and (c) makes it possible to improve the light-fastness in quenched state because the electron donating compound has a weak interaction with the ultraviolet-absorbing electron accepting compound (b) and the light-fastness providing agent (d) while being dissolved in the discoloration temperature adjustor (c). Moreover, the addition of the component (e) makes it possible to further improve the light-fastness of the reversible thermochromic composition.

Further, the provision of a layer of light stabilizer or metallic luster pigment on the surface of the foregoing layer formed by the reversible thermochromic composition makes it possible to further improve the light-fastness of the reversible thermochromic composition in quenched state.

Discoloration Sensitivity Test

The test specimen 2 comprising the reversible thermochromic composition of Example 2 made of the components (a), (b) and (c) of the invention and the test specimen 26 comprising the reversible thermochromic composition 21 of Comparative Example 5 having a large amount of the component (e) added to conventional reversible thermochromic composition were subjected unirradiated to discoloration test on heating and cooling in the following manner. The resulting discoloration behavior was then plotted on a graph to determine discoloration sensitivity.

The various test specimens were each stuck to a Type TC-3600 color difference meter (produced by Tokyo Denshoku K.K.) at a predetermined position. The prints were then each heated and cooled at a rate of 10° C./min within a temperature range of 50° C.

The brightness value indicated on the color difference meter at various temperatures were then plotted on a graph to draw color density-temperature curve. Thus, various values of $T_1$ (full color development temperature), $T_2$ (color development starting temperature), $T_3$ (quenching starting temperature) and $T_4$ (full quenching temperature) were determined.

FIG. 1 indicates the color density-temperature curve of the test specimen 2 of Example 2. The color density-temperature curve shows that $T_1$ is 15° C., $T_2$ is 18° C., $T_3$ is 28° C. and $T_4$ is 32° C.

Figure 2:
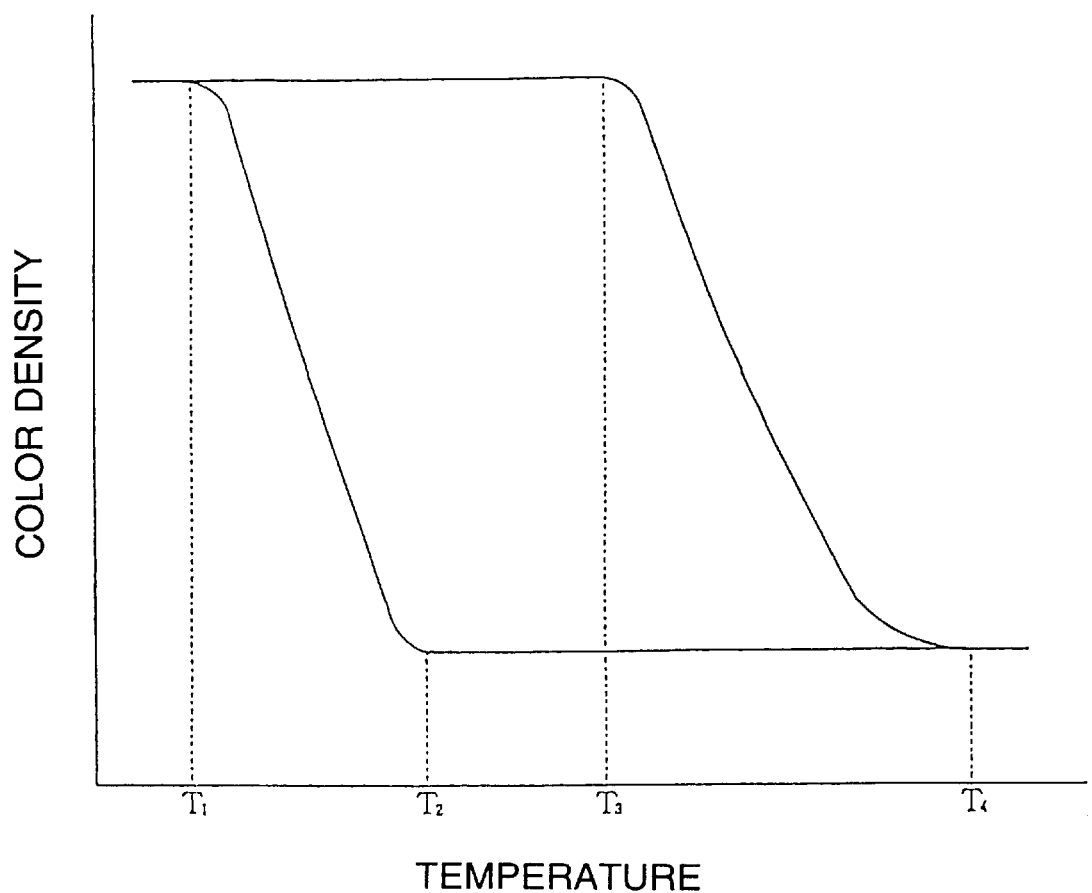
FIG. 2 is a graph illustrating hysteresis characteristics on color density-temperature curve of a conventional reversible thermochromic composition.

FIG. 2 indicates the color density-temperature curve of the test specimen 26 of Comparative Example 5. The color density-temperature curve shows that $T_1$ is 12° C., $T_2$ is 18° C., $T_3$ is 22° C. and $T_4$ is 32° C.

The smaller the difference between $T_2$ and $T_1$ ($T_2-T_1$) and the difference between $T_4$ and $T_3$ ($T_4-T_3$) are, the more sensitivity the reversible thermochromic composition discolors and the better is discoloration sensitivity.

The temperature difference ($T_2-T_1$) and ($T_4-T_3$) of the test specimen 2 are 3° C. and 4° C., respectively. On the contrary, the temperature difference ($T_2-T_1$) and ($T_4-T_3$) of the test specimen 26 are 6° C. and 10° C., respectively. This demonstrates that the reversible thermochromic composition of the invention has a high discoloration sensitivity.

Besides the light-fastness test in quenched state and discoloration test on the foregoing reversible thermochromic compositions of the invention and the conventional reversible thermochromic compositions, the reversible thermochromic compositions of the invention were each subjected to light-fastness test in color-developed state.

As test specimens there were used the test specimen 2 comprising the reversible thermochromic composition of Example 2 made of the components (a), (b) and (c), the test specimens 12 to 14 comprising the reversible thermochromic compositions of Examples 12 to 14 made of the components (a), (b), (c) and (d), the test specimen 15 of Example 15 comprising the reversible thermochromic composition made of the components (a), (b), (c), (d) and (e), and the test specimens 20 and 21 having a layer of light stabilizer and/or metallic luster pigment (f) provided on the reversible thermochromic layer formed by the reversible thermochromic composition of Example 15 made of the compositions (a), (b), (c), (d) and (e).

The test specimens 2 and 12 to 15 were each irradiated with light from xenon arc lamp at four points for 5 hours, 10 hours, 15 hours and 20 hours for measurement.

The test specimens 20 and 21 were each irradiated with light from xenon arc lamp at four points for 10 hours, 20 hours, 30 hours and 40 hours for measurement.

Table 26 shows the results of light-fastness test on the test specimens 2 and 12 to 15 in color-developed state.

TABLE 26

| Test specimen | Composition | Constituent element | Unirradiated | 5 hours | 10 hours | 15 hours | 20 hours |
|---|---|---|---|---|---|---|---|
| 2 | Reversible thermochromic composition 2 | a, b, c | 100% | 55% | 28% | 19% | 15% |
| 12 | Reversible thermochromic composition 12 | a, b, c, d | 100% | 97% | 93% | 90% | 85% |
| 13 | Reversible thermochromic composition 13 | a, b, c, d | 100% | 100% | 98% | 96% | 94% |
| 14 | Reversible thermochromic composition 14 | a, b, c, d | 100% | 100% | 99% | 97% | 95% |
| 15 | Reversible thermochromic composition 15 | a, b, c, d, e | 100% | 100% | 100% | 98% | 96% |

Table 27 shows the results of light-fastness test in color-developed state on the test specimens 20 and 21.

TABLE 27

| Test specimen | Composition | Constituent element | Unirradiated | 10 hours | 20 hours | 30 hours | 40 hours |
|---|---|---|---|---|---|---|---|
| 20 | Reversible thermochromic composition 15 | a, b, c, d, e, f (layer of metallic luster pigment) | 100% | 100% | 100% | 100% | 99% |
| 21 | Reversible thermochromic composition 15 | a, b, c, d, e f (layer of light stabilizer and metallic luster pigment) | 100% | 100% | 100% | 100% | 99% |

The percent color density retention in the foregoing results of light-fastness test will be described hereinafter.

The various test specimens were each measured for density stimulation value (X value) unirradiated or after irradiated for a predetermined period of time using a Type TC-3600 color difference meter (produced by Tokyo Denshoku K.K.).

The percent color density was calculated by the following equation:

% Color density retention=[100−stimulation value (X) after irradiated]/[100−stimulation value (X) before irradiated]×100

Referring to light-fastness in color-developed state, as indicated by the percent color density retention in the table above, the reversible thermochromic composition having the component (d) added thereto exhibits a better light-fastness in color-developed state than the reversible thermochromic composition comprising the components (a), (b) and (c). The further provision of the layer of light stabilizer and/or metallic luster pigment (f) gives a better light-fastness in color-developed state.

As can be seen in the foregoing results of light-fastness test in color-developed state, the addition of the component (d) to the reversible thermochromic composition comprising the components (a), (b), and (c) makes it possible to improve the light-fastness during color development.

Examples of ink, fiber treatment, coating compound, cosmetics and molding resin composition made of microcapsuled pigment having the reversible thermochromic composition of the invention incorporated therein will be described hereinafter.

EXAMPLE 17
Ink for Writing Utensils Containing Reversible Thermochromic Composition 2 and Writing Utensils Comprising Same 25.0 parts by weight of a microcapsuled pigment having the reversible thermochromic composition 2 incorporated therein were uniformly dispersed in a vehicle consisting of 5.0 parts by weight of glycerin, 0.7 parts by weight of a mildewproofing agent, 0.1 parts by weight of a silicone-based anti-foaming agent and 68.2 parts by weight of water to obtain a reversible thermochromic aqueous ink.

An ink-absorbing material having a polyester sliver coated with a synthetic resin film was then impregnated with the foregoing reversible thermochromic aqueous ink composition. The ink-absorbing material was then received in a cylinder in such an arrangement that it was connected to a pen formed by a polyester resin fiber mounted on the forward end of the cylinder to prepare writing utensils.

The writing made by the writing utensils became colorless when heated to a temperature of not lower than 32° C. but assumed pink at a temperature of not higher than 15° C.

The writing exhibited an improved light-fastness and a high discoloration sensitivity similarly to the light-fastness test specimen 2.

EXAMPLE 18
Screen Ink Containing Reversible Thermochromic Composition 8 and Sheet Comprising Same 40.0 parts by weight of a microcapsuled pigment having the reversible thermochromic composition 8 incorporated therein were uniformly dispersed in a vehicle consisting of 50.0 parts by weight of an ethylene-vinyl acetate copolymer resin emulsion, 3.0 parts by weight of an anti-foaming agent, 1.0 part by weight of a thickening agent (sodium alginate), 3.0 parts by weight of a leveling agent, and 1.0 part by weight of a mildewproofing agent to obtain a reversible thermochromic screen ink.

The foregoing screen ink was then printed on a support obtained by applying an adhesive to a synthetic white paper having a thickness of 80 μm, and then laminating a polyethylene foam having a thickness of 1 mm thereon using a 150-mesh screen made of polyester to form a reversible thermochromic layer thereon. Thus, a reversible thermochromic sheet was obtained.

The foregoing sheet assumed white on the whole surface thereof when heated to a temperature of not lower than 32° C. but assumed blue at a temperature of not higher than 15° C.

The foregoing sheet exhibited an improved light-fastness and an excellent discoloration sensitivity similarly to the light-fastness test specimen 8.

EXAMPLE 19
Fiber Treatment Containing Reversible Thermochromic Composition 13 and Stuffed Doll Comprising Same 20.0 parts by weight of a microcapsuled pigment having the reversible thermochromic composition 13 incorporated therein were uniformly dispersed in a vehicle consisting of 80.0 parts by weight of an acrylic acid ester resin emulsion, 0.5 parts by weight of an anti-foaming agent, and 0.5 parts by weight of a leveling agent to obtain a reversible thermochromic aqueous coating solution.

100.0 parts by weight of a raw cotton of polyacrylonitrile with 7 denier having a length of 70 mm were then dipped in the foregoing reversible thermochromic aqueous coating solution. Thereafter, the raw cotton was subjected to centrifugal separation so that excess coating solution was removed, and then dried at a temperature of 90° C. for 10 minutes to obtain a raw cotton of reversible thermochromic polyacrylonitrile.

The foregoing raw cotton of reversible thermochromic polyacrylonitrile was then carded to form a sliver. The sliver thus formed was knitted by a hi-pile knitting machine. The knitted material was sheared to obtain a reversible thermochromic hi-pile cloth having a pile length of 20 mm.

The reversible thermochromic hi-pile cloth thus obtained was then subjected to sewing to obtain a reversible thermochromic stuffed doll of bear.

The stuffed doll thus obtained assumed white when heated to a temperature of not lower than 32° C. but assumed pink at a temperature of not higher than 15° C.

The stuffed doll exhibited an improved light-fastness and an excellent discoloration sensitivity similarly to the light-fastness test specimen 13.

EXAMPLE 20
Spray Coating Compound Containing Reversible Thermochromic Composition 15 and Miniaturized Car Comprising Same 25.0 parts by weight of a microcapsuled pigment having the reversible thermochromic composition 15 incorporated therein were uniformly dispersed in a vehicle consisting of 50.0 parts by weight of an acrylic resin solution (solid content: 40%; toluene: 60%), 49.0 parts by weight of methyl isobutyl ketone and 1.0 part by weight of a leveling agent. The dispersion thus obtained was then filtered through a 180-mesh stainless steel screen to obtain a reversible thermochromic spray coating compound.

The foregoing reversible thermochromic spray coating compound was sprayed onto a white miniaturized car through a spray gun having an aperture diameter of 0.6 mm, and then dried to form a reversible thermochromic layer thereon. Onto the reversible thermochromic layer was then sprayed a metallic luster spray coating compound having 1.5 parts by weight of a metallic luster pigment (trade name: Iriodin 219, produced by Merck Japan Ltd.) uniformly dispersed in a vehicle consisting of 50.0 parts by weight of an acrylic resin solution (solid content: 40%; toluene: 60%), 49.0 parts by weight of toluene and 1.0 part by weight of a leveling agent. The coated miniaturized car was then dried to obtain a reversible thermochromic miniaturized car having a metallic luster pigment layer provided thereon.

The foregoing miniaturized car assumed white when heated to a temperature of 32° C. but assumed metallic pink at a temperature of not higher than 15° C.

The foregoing miniaturized car exhibited an improved light-fastness and an excellent discoloration sensitivity similarly to the light-fastness test specimen 20.

EXAMPLE 21
Cosmetic Containing Reversible Thermochromic Composition 15 and False Nail Comprising Same 15.0 parts by weight of a microcapsuled pigment comprising the reversible thermochromic composition 15 incorporated therein were stirred in a vehicle consisting of 40.0 parts by weight of an acrylic polyol resin solution (solid content: 50%; xylene: 50%), 30.0 parts by weight of xylene, 30.0 parts by weight of methyl isobutyl ketone and 10.0 parts by weight of an isocyanate-based hardener to obtain an oil-based spray cosmetic for reversible thermochromic false nail.

The foregoing oil-based spray cosmetic for reversible thermochromic false nail was sprayed onto the surface of a false nail made of acetyl cellulose resin through a spray gun having an aperture diameter of 0.6 mm, and then dried to form a reversible thermochromic layer thereon. Onto the reversible thermochromic layer was then sprayed a top coating cosmetic obtained by uniformly stirring 1.5 parts by weight of a metallic luster pigment (trade name: Iriodin 219, produced by Merck Japan Ltd.) in a vehicle consisting of 50.0 parts by weight of an acrylic resin solution (solid content: 50%; xylene: 50%), 45 parts by weight of cyclohexanone, 3.0 parts by weight of a leveling agent, 1.0 part by weight of an anti-foaming agent and 1.0 part by weight of a viscosity modifier to form a layer containing a light stabilizer and a noble metal luster pigment. Thus, a reversible thermochromic false nail was obtained.

The foregoing false nail became colorless when heated to a temperature of not lower than 32° C. but assumed metallic pink at a temperature of not higher than 15° C.

The foregoing false nail exhibited an improved light-fastness and an excellent discoloration sensitivity similarly to the light-fastness test specimen 21

EXAMPLE 22
Molding Resin Composition Containing Reversible Thermochromic Composition 2 and Molded Product Comprising Same 40.0 parts by weight of a microcapsuled pigment comprising the reversible thermochromic composition 2 incorporated therein were blended with 1,000.0 parts by weight of a low density polyethylene resin (melt flow rate: 1.3) and 0.5 parts by weight of a metallic soap-based lubricant. The mixture was then subjected to uniform dispersion by a tumbler mixer to obtain a molding resin composition. The molding resin composition thus obtained was then processed through a extruder at a cylinder temperature of 170° C. and a forward end die temperature of 180° C. to obtain a reversible thermochromic polyethylene resin pellet.

The foregoing molding resin composition was then blow-molded in a goldfish molded at a cylinder temperature of 160° C. to obtain a goldfish-shaped reversible thermochromic hollow molded product.

The foregoing molded product assumed white when heated to a temperature of 32° C. but assumed pink at a temperature of not higher than 15° C.

The foregoing molded product exhibited an improved light-fastness and an excellent discoloration sensitivity similarly to the light-fastness test specimen 2.

EXAMPLE 23
Molding Resin Composition Containing Reversible Thermochromic Composition 13 and Filament Comprising Same 50.0 parts by weight of a microcapsuled pigment comprising the reversible thermochromic composition 13 incorporated therein were blended with 1,000.0 parts by weight of nylon 12 resin (melting point: 178° C.). The mixture was then subjected to uniform dispersion by a Henschel mixer to obtain a molding resin composition. The molding resin composition was then processed through an extruder at a cylinder temperature of 190° C. and a forward end die temperature of 200° C. to obtain a reversible thermochromic nylon 12 resin pellet.

The foregoing molding resin composition was then melt-spun at a cylinder temperature of 190° C. and a die temperature of 200° C. to obtain a reversible thermochromic filament.

The filament was then planted on the head of a doll.

The foregoing filament became colorless when heated to a temperature of not lower than 32° C. but assumed pink at a temperature of not higher than 15° C.

The foregoing filament exhibited an improved light-fastness and an excellent discoloration sensitivity similarly to the light-fastness test specimen 13.

EXAMPLE 24
Molding Resin Composition Containing Reversible Thermochromic Composition 13 and Composite Filament Comprising Same 5 parts by weight of a microcapsuled pigment comprising the reversible thermochromic composition 13 incorporated therein, 1 part by weight of a dispersant and 94 parts by weight of nylon 12 resin having a melting point of 180° C. were melt-kneaded through an extruder at a temperature of 200° C. to obtain a core-forming reversible thermochromic nylon 12 resin pellet.

Separately, 95 parts by weight of nylon 12 resin having a melting point of 180° C. and 5.0 parts by weight of 2-(3,5-di-t-amyl-2-hydroxyphenyl)benzotriazole as a light stabilizer were melt-kneaded through an extruder to obtain a sheath-forming nylon 12 resin pellet.

The foregoing reversible thermochromic nylon 12 resin pellet was supplied into a core forming extruder while the sheath-forming nylon 12 resin pellet was supplied into a sheath forming extruder. The two resin pellets were each extruded at a melting temperature of 200° C. and then spun through 18 ejection holes from a composite fiber spinning machine. The thread thus spun was then wound at a draw ratio of 3 to obtain a reversible thermochromic filament with 1,260 denier consisting of 18 filaments.

The foregoing composite filament became colorless when heated to a temperature of not lower than 32° C. but assumed pink at a temperature of not higher than 15° C.

The foregoing composite filament exhibited an improved light-fastness and an excellent discoloration sensitivity similarly to the light-fastness test specimen 13.

The discoloration temperature of the reversible thermochromic composition of the invention and products comprising same can be freely adjusted even the kind of the electron donating compound and electron accepting compound to be used in combination remain the same. Accordingly, the reversible thermochromic composition of the invention exhibits an remarkably improved light-fastness, particularly during quenching, and better discoloration sensitivity.

While the invention has been described in detail and with reference to specific embodiments thereof, it will be apparent to one skilled in the art that various changes and modifications can be made therein without departing from the spirit and scope thereof.

This application is based on Japanese patent application No. 2000-275649 filed on Aug. 9, 2000, the entire contents thereof being hereby incorporated by reference.

What is claimed is:

1. A reversible thermochromic composition, which comprises
   (a) an electron donating compound,
   (b) an electron accepting compound having ultraviolet absorbing capacity which is presented by the following general formula I:

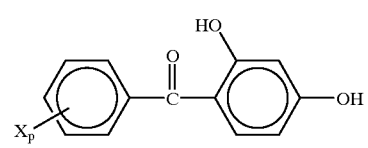

wherein X represents —$C_nH_{2n+1}$ or —$OC_mH_{2m+1}$; m represents an integer of from 1 to 9; n represents an integer of from 1 to 10; and p represents an integer of from 1 to 3, and
   (c) a discoloration temperature adjustor.

2. A reversible thermochromic composition, which comprises
(a) an electron donating compound,
(b) an electron accepting compound having ultraviolet absorbing capacity which is represented by the following general formula I:

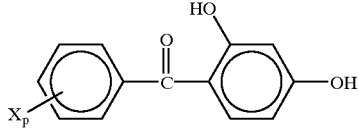

wherein X represents —$C_nH_{2n+1}$ or —$OC_mH_{2m+1}$; m represents an integer of from 1 to 9; n represents an integer of from 1 to 10; and p represents an integer of from 1 to 3,
(c) a discoloration temperature adjustor, and
(d) an electron accepting light-fastness providing agent represented by the following general formula II:

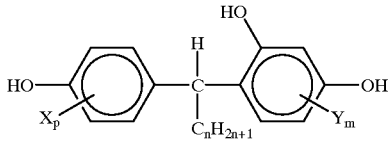

wherein n represents an integer of from 5 to 17 (straight-chain and branched); X represents a $C_1$–$C_4$ straight-chain or branched hydrocarbon or halogen; Y represents a $C_1$–$C_4$ straight-chain or branched hydrocarbon or halogen; p represents an integer of from 0 to 3; and m represents an integer of from 0 to 3.

3. A reversible thermochromic composition, which comprises
(a) an electron donating compound,
(b) an electron accepting compound having ultraviolet absorbing capacity represented by the following general formula I:

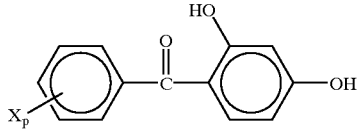

wherein X represents —$C_nH_{2n+1}$ or —$OC_mH_{2m+1}$; m represents an integer of from 1 to 9; n represents an integer of from 1 to 10; and p represents an integer of from 1 to 3, (c) a discoloration temperature adjustor,
(d) an electron accepting light-fastness providing agent represented by the following general formula II:

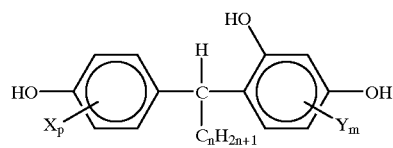

wherein n represents an integer of from 5 to 17 (straight-chain and branched); X represents a $C_1$–$C_4$ straight-chain or branched hydrocarbon or halogen; Y represents a $C_1$–$C_4$ straight-chain or branched hydrocarbon or halogen; p represents an integer of from 0 to 3; and m represents an integer of from 0 to 3, and (e) a light stabilizer.

4. The reversible thermochromic composition according to any one of claims 1 to 3, which further comprises a microcapsule incorporating said reversible thermochromic composition therein.

5. The reversible thermochromic according to any one of claims 1 to 3, which further comprises a color developer blended in said reversible thermochromic composition having an improved light-fastness.

6. The reversible thermochromic composition according to claim 5, wherein said color developer is a binder.

7. A molding resin composition comprising a synthetic resin and a reversible thermochromic composition according to any one of claims 1 to 3 blended therein.

8. A reversible thermochromic yarn comprising a reversible thermochromic composition according to any one of claims 1 to 3 and a thermoplastic resin.

9. A reversible thermochromic layer according to any one of claims 1 to 3, which further comprises (f) a layer of light stabilizer and/or metallic luster pigment provided on the surface of a layer formed by a reversible thermochromic composition.

* * * * *